US006306610B1

United States Patent
Bawendi et al.

(10) Patent No.: US 6,306,610 B1
(45) Date of Patent: *Oct. 23, 2001

(54) BIOLOGICAL APPLICATIONS OF QUANTUM DOTS

(75) Inventors: Moungi G. Bawendi, Boston, MA (US); Frederic V. Mikulec, La Jolla, CA (US); Vikram C. Sundar, Stoneham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/397,436

(22) Filed: Sep. 17, 1999

Related U.S. Application Data

(63) Continuation-in-part of application No. 09/160,454, filed on Sep. 24, 1998.
(60) Provisional application No. 60/100,947, filed on Sep. 18, 1998, and provisional application No. 60/101,046, filed on Sep. 18, 1998.

(51) Int. Cl.[7] .................................................. G01N 33/53
(52) U.S. Cl. ............... 435/7.1; 435/6; 436/172; 436/546; 436/2; 250/307; 250/302; 250/459.1; 356/317; 252/301.7; 252/301.33; 252/301.36; 378/47; 422/82.08
(58) Field of Search ................................... 436/172, 546, 436/2; 435/6, 7.1; 250/307, 302, 459.1; 356/317; 252/301.7, 301.33, 301.36; 378/47; 422/82.08

(56) References Cited

U.S. PATENT DOCUMENTS

| | | | |
|---|---|---|---|
| 3,996,345 | 12/1976 | Ullman et al. | 424/12 |
| 4,637,988 | 1/1987 | Hinshaw et al. | 436/546 |
| 4,777,128 | 10/1988 | Lippa | 435/5 |
| 5,262,357 | 11/1993 | Alivisatos et al. | 437/233 |
| 5,293,050 | 3/1994 | Chapple-Sokol et al. | 257/17 |
| 5,304,786 | 4/1994 | Pavlidis et al. | 235/462 |
| 5,354,707 | 10/1994 | Chapple-Sokol et al. | 437/106 |
| 5,395,791 | 3/1995 | Cheng et al. | 437/105 |
| 5,422,489 | 6/1995 | Bhargava | 250/488.1 |
| 5,492,080 | 2/1996 | Ohkawa et al. | 117/108 |
| 5,499,260 | 3/1996 | Takahashi et al. | 372/46 |
| 5,505,928 | 4/1996 | Alivisatos et al. | 423/299 |

(List continued on next page.)

FOREIGN PATENT DOCUMENTS

| | | |
|---|---|---|
| WO 95/29473 | 11/1995 | (WO) . |
| Wo 98/04740 | 2/1998 | (WO) . |
| WO 98/19963 | 5/1998 | (WO) . |
| WO 98/33070 | 7/1998 | (WO) . |
| WO 98/36376 | 8/1998 | (WO) . |
| WO 98/46372 | 10/1998 | (WO) . |
| WO 99/19515 | 4/1999 | (WO) . |
| WO 00/27365 | 5/2000 | (WO) . |
| WO 00/27436 | 5/2000 | (WO) . |
| WO 00/28088 | 5/2000 | (WO) . |
| WO 00/28089 | 5/2000 | (WO) . |

OTHER PUBLICATIONS

Alivisatos et al., "Semiconductor Clusters, Nanocrystals, and Quantum Dots," *Science*, 271:933–937, 1996.

(List continued on next page.)

*Primary Examiner*—Long V. Le
*Assistant Examiner*—Minh-Quan F. Pham
(74) *Attorney, Agent, or Firm*—Fish & Richardson P.C.

(57) ABSTRACT

The present invention provides a composition comprising fluorescent semiconductor nanocrystals associated to a compound, wherein the nanocrystals have a characteristic spectral emission, wherein said spectral emission is tunable to a desired wavelength by controlling the size of the nanocrystal, and wherein said emission provides information about a biological state or event.

57 Claims, 9 Drawing Sheets

U.S. PATENT DOCUMENTS

| | | | |
|---|---|---|---|
| 5,515,393 | 5/1996 | Okuyama et al. | 372/45 |
| 5,525,377 | 6/1996 | Gallagher et al. | 427/512 |
| 5,537,000 | 7/1996 | Alivisatos et al. | 313/506 |
| 5,541,948 | 7/1996 | Krupke et al. | 372/41 |
| 5,565,324 | 10/1996 | Still et al. | 435/6 |
| 5,585,640 | 12/1996 | Huston et al. | 250/483.1 |
| 5,625,456 | 4/1997 | Lawandy | 356/376 |
| 5,674,698 | 10/1997 | Zarling et al. | 435/7.92 |
| 5,721,099 | 2/1998 | Still et al. | 435/6 |
| 5,736,330 | 4/1998 | Fulton | 435/6 |
| 5,747,180 | 5/1998 | Miller et al. | 372/41 |
| 5,751,018 | 5/1998 | Alivisatos et al. | 257/64 |
| 5,770,299 | 6/1998 | Dannenhauer et al. | 428/195 |
| 5,789,162 | 8/1998 | Dower et al. | 435/6 |
| 5,985,353 | 11/1999 | Lawton et al. | 427/2.13 |
| 5,990,479 | 11/1999 | Weiss et al. | 250/307 |
| 6,114,038 | 9/2000 | Castro et al. | 428/402.24 |

OTHER PUBLICATIONS

Alivisatos et al, "Organization of 'nanocrystal molecules' using DNA," *Nature,* 382:609–611, Aug. 15, 1996.

Baldwin et al., "Synthesis of a Small Molecule Combinatorial Library Encoded with Molecular Tags," *J. Am. Chem. Soc.,* 117:5588–5589, May 24, 1995.

Beverloo et al., "Preparation and Microscopic Visualization of Multicolor Luminescent Immunophosphors," *Cytometry,* 13:561–570, 1992.

Bruchez et al., "Semiconductor nanocrystals as fluorescent piological for biology," *Cytometry,* Supplement 9, p. 26, Mar., 1998.

Bruchez et al., "Luminescent Semiconductor Nanocrystals: Intermitten Behavior and Use as Fluorescent Probes," Doctoral Dissertation, University of California, Jul. 13, 1999.

Cook, "Scintillation Proximity Assay: A Versatile High-Throughput Screening Technology," *Drug Discovery Today,* 1:287–294, 1997.

Czarnik, "Encoding methods for combinatorial chemistry," *Curr. Opin. Chem. Biol.,* 1(1):60, 1997.

Gao et al., "Strongly Photoluminescent CdTe Nanocrystals by Proper Surface Modification," *J. Phys. Chem.,* 102:8360–8363, 1998.

Jarvis et al., "Solution Synthesis and Photoluminescence Studies of Small Crystallites of Cadmium Telluride," *Mat. Res. Soc. Symp. Proc.,* 272:229–234, 1992.

Kagan et al., "Electronic Energy Transfer in CdSe Quantum Dot Solids," *Physical Review Letters,* 76:1517–1520, 1996.

Kagan et al., "Long–range resonance transfer fo electronic excitations in close–packed CdSe quantum–dot solids, "*Physical Review Letters,* 54:8633–8643, Sep. 15, 1996.

Lee et al., "Surface Derivatization of Nanocrystalline CdSe Semiconductors," *Mat. Res. Soc. Symp. Proc.,* 452:323–328, 1997.

Michael et al., "Randomly Ordered Addressable High–Density Optical Sensor Arrays," *Analytical Chemistry,* 70:1242–1248, Apr. 1, 1998.

Mikulec et al., "Synthesis and Characterization of Higly Luminescent (CdSe)ZnS Quantum Dots," Materials Research Society Symposium, 452:359–364, 1997.

Moran, "Radio Frequency Tag Encoded Combinatorial Library Method for the Discovery of Tripeptide–Substituted Cinnamic Acid Inhibitors of the Protein Tyrosine Phosphatase PTPIB," *J. Am. Chem. Soc.,* 117:10787–10788, 1995.

Müllenborn et al., "Characterization of Solution–Synthesized CdTe and HgTe," *Applied Physics,* 56:317–321, 1993.

Nicolaou et al., "Radiofrequency Encoded Combinatorial Chemistry," *Ingew. Chem. Int. Ed. Engl.* 34(20):2289–2291, 1995.

Pehnt et al., "Nanoparticle Precursor Route to Low–Temperature Spray Deposition of CdTe Thin Films," *Appl. Phys. Lett.,* 67(15):2176–2178, 1995.

Peng et al., "Epitaxial Growth of Highly Luminescent CdSe/CdS Core/Shell Nanocrystals with Photostability and Electronic Accessibility," *J. Am. Chem. Soc.,* 119:7019–7029, 1997.

Peng et al., "Synthesis and Isolation of a Homodimer of Cadmium Selenide Nanocrystals," *Angewandte Chemie,* 36:145–147, 1997.

Plunkett et al., "Combinatorial Chemistry and New Drugs," *Scientific American,* 276(4):68–73, Apr. 1997.

Schröck et al., "Multicolor Spectral Karyotyping of Human Chromosomes," *Science,* 273:494–497, 1996.

Steigerwald et al., "Surface Derivatization and Isolation of Semiconductor Cluster Molecules," *J. Am. Chem. Soc.,* 110:3046–3050, 1988.

Wade, "In the Hunt for Useful Genes, a Lot Depends on 'Snips'", *New York Times,* C1, C5, Aug. 11, 1998.

Wang et al., "Large–Scale Identification, Mapping, and Genotyping of Single–Nucleotide Polymorphisms in the Human Genome," *Science,* 280:1077–1082, May 15, 1988.

Winzeler et al., "Direct Allelic Variation Scanning of the Yeast Genome", *Science,* 281:1194–1197, Aug. 21, 1998.

Zhang et al., "Novel Flow Cytometry Compensation Standards: Internally Stained Fluorescent Microspheres With Matched Emission Spectra and Long–Term Stability," *Cytometry,* 33:244–248, Oct. 1, 1998.

Spanhel et al., "Photochemisty of Colloidal Semiconductors. Surface Modification and Stability of Strong Luminescing CdS Particles" *J. Am. Chem. Soc.* 109(19):5649–5655, 1987.

Kortan et al., "Nucleation and Growth of CdSe on ZnS Quantum Crystallite Seeds, and Vice Versa, in Inverse Micelle Media" *J. Am Chem. Soc.* 112:1327–1332, 1990.

Coffer et al., "Characterization of quantum–confined CdS Nanocrystallites stabilized by deoxyribonucleic acid (DNA)" *Nanotechnology* 3:69–76, 1992.

Murray et al., "Synthesis and Characterization of Nearly Monodisperse CdE (E=S, Se, Te) Semicondutor Nanocrystallites" *J. Am. Chem. Soc.* 115(19):8706–8715, 1993.

Whitesell et al., "Directionally Aligned Helical Peptides on Surfaces" *Science* 261:73–76, Jul. 1993.

Rajh et al., "Synthesis and Characterization of Surface–Modified Colloidal CdTe Quantum Dots" *J. Phys. Chem.* 97:11999–12003, Nov. 1993.

Colvin et al., "Light–emitting diodes made from cadmium selenide nanocrystals and a semiconducting polymer" *Nature* 370(6488):354–357, Aug. 4, 1994.

Lawless et al., "Bifunctional Capping of CdS Nanoparticles and Bridging to TiO2" *J. Phys. Chem.* 99:10329–10335, 1995.

Dabbousi et al., "Electroluminescence from CdSe quantum–dot/polymer composites" *Appl. Phys. Lett.* 66(11):1316–1318, Mar. 13, 1995.

Alivisatos, "Perspectives on the Physical Chemistry of Semiconductor Nanocrystals" *J. Phys. Chem.* 1996(100):13226–13239, 1996.

Danek et al., "Synthesis of Luminescent Thin–Film CdSe/ZnSe Quantum Dot Composites Using CdSe Quantum Dots Passivated with an Overlayer of ZnSe" *Chem. Mater.* 8(1):173–180, 1996.

Liz–Marzan et al., "Synthesis of Nanosized Gold–Silica Core–Shell Particles" *Langmuir* 12:4329–4335, 1996.

Matsumoto et al., "Preparation of Monodisperse CdS Nanocrystals by Size Selective Photocorrosion" *J. Phys. Chem.* 100(32):13781–13785, 1996.

Rogach et al., "Synthesis and characterization of Thiol–Stabilized CdTe Nanocrystals" *Ber. Bunsenges. Phys. Chem.* 100(11):1772–2778, 1996.

Hines et al., "Synthesis and Characterization of Strongly Luminescing ZnS–Capped CdSe Nanocrystals" *J. Phys. Chem.* 100:468–471, Jan. 1996.

McGall et al., "Light–directed synthesis of high–density oligonucleotide arrays using semiconductor photoresists" *Proc. Natl. Acad. Sci. USA* 93:13555–13560, Nov. 1996.

Chee et al., "Accessing Genetic Information with High–Density DNA Arrays" *Science* 274(5287):610–614, Oct. 25, 1996.

Empedocles et al, "Photoluminescence Spectroscopy of Single CdSe Nanocrystallite Quantum Dots" *Phys. Rev. Lett.* 77(18):3873–3876, Oct. 1996.

Nirmal et al., "Fluorescence Intermittency in single Cadmium Selenide Nanocrystals" *Nature* 383:802–804, Oct. 1996.

Egner et al., "Tagging in combinatorial chemistry: the use of coloured and fluorescent bads" *Chem. Commun.*, 735–736, 1997.

Gan et al., "Enhanced Photoluminescence and Characterization of Mn–Doped ZnS Nanocrystallites Synthesized in Microemulsion" *Langmuir* 1997(13):6427–6431, 1997.

Empedocles et al., "Quantum–Confined Stark Effect in Single CdSe Nanocrystallite Quantum Dots" *Science* 278:2114–2117, Dec. 1997.

Fodor, "Techwire" *Science* 277(5324):393–395, Jul. 18, 1997.

Kuno et al., "The band edge luminescence of surface modified CdSe nanocrystallites: Probing the luminescing state" *J. Chem. Phys.* 106(23):9869–9882, Jun. 1997.

Dabbousi, et al., "(CdSe)ZnS core–shell quantum dots: synthesis and characterization of a size series of highly luminescent nanocrystallites" *J. of Phys. Chem. B* 101(46):9463–9475, Nov. 13, 1997.

Guha et al., "Hybrid organic–inorganic semiconductor–based light–emitting diodes" *J. Appl. Phys.* 82(8):4126–4128, Oct. 15, 1997.

Fox et al., "Fluorescence and Redox Activity of Probes Anchored through an Aminotrithiol to Polycrystalline Gold" *Langmuir* 14:816–820, 1998.

Mikulec et al., "Fluorescent semiconductor nanocrystallites derivatized with biomolecules" *Amer. Chem. Soc. Nat'l Meeting,* Boston, MA, Aug. 24, 1998.

Service, "Semiconductor Beacons Light Up Cell Structures" *Science* 281:19930–1931, Sep. 25, 1998.

Jacoby, "Quantum dots meet biomolecules" *C&E News* :8, Sep. 28, 1998.

Bruchez et al., "Semiconductor Nanocrystals as Fluorescent Biological Lables" *Science* 281:2013–2016, Sep. 1998.

Chan et al., "Quantum Dot Bioconjugates for Ultrasensitive Nonisotopic Detection" *Science* 281:2016–2018, Sep. 1998.

Lett, "Color–Coding Quanntum Dots Debut with Promising Careers In Clinical Diagnostics Field" :1–2, Sep. 25, 1998.

Mahtab et al., "Protein–sized quantum dot luminescence can distinguish between 'straight', 'bent', and 'kinked' oligonucletides", *Am. Chem. Soc.,* 117:9099–9100, 1995.

Mahtab et al., "Preferential–absorption of a 'kinked' DNA to a newtral curved surface: comparison to and implications for nonspecific DNA–protein interactions," *J. Am. Chem. Soc.,* 118:7028–7032, 1996.

Murphy et al., "Quantum dots as inorganic DNA–binding proteins," *Mat. Res. Soc. Symp.,* 452:597–600, 1997.

Bawendi et al., "Luminescence properties of CdSe quantum crystallites: resonance between interior and surface localized states," *J. Chem. Phys.,* 96(2):946–954, 1992.

Correa–Duarte et al., "Stabilization of CdS semiconductor nanoparticles against photodegradation by silica coating procedure," *Chem. Phys. Lett.,* 286:497–501, 1998.

SINGLE-QUANTUM DOT LABELED IMMUNOASSAY

MULTI-QUANTUM DOT LABELED, PARALLEL IMMUNOASSAY

BIOLOGICAL APPLICATIONS OF QUANTUM DOTS

This application is related to the following commonly owned applications which are incorporated in their entirety by reference: U.S. application Ser. No. 09/397,432 entitled "Inventory Control" by Bawendi et al. filed Sep. 17, 1999; U.S. application Ser. No. 09/160,458 entitled "Inventory Control," by Bawendi et al. filed Sep. 24, 1998; U.S. application Ser. No. 09/397,428 entitled "Water-Soluble Fluorescent Semiconductor Nanocrystals" by Bawendi et al. filed Sep. 17, 1999 and U.S. application Ser. No. 09/156,863, entitled "Water-Soluble Luminescent Nanocrystals," by Bawendi et al., filed on Sep. 18, 1998. This application claims priority under 35 U.S.C. 119(e) to the provisional U.S. application Ser. No. 60/100,947 entitled "Detection of Compounds and Interactions in Biological Systems Using Quantum Dots," by Bawendi et al., filed Sep. 18, 1998 hereby incorporated in its entirety by reference and to the provisional U.S. application Ser. No. 60/101,046 entitled "Inventory Control" by Bawendi et al. filed Sep. 18, 1998 hereby incorporated in its entirety by reference. This application is a continuation-in-part of U.S. application Ser. No. 09/160,454, filed Sep. 24, 1998, the disclosure of which is incorporated by reference herein.

This invention was made with government support under Grant Number DMR-9400334 awarded by the National Science Foundation. The government has certain rights in the invention.

FIELD OF THE INVENTION

This invention relates generally to a compositions for use in biological applications. More specifically, the invention relates to compositions comprising fluorescent semiconductor nanocrystals associated with compounds for use in biological applications, such as affinity molecules capable of interacting specifically with biological targets, and to methods of using such compounds.

BACKGROUND OF THE INVENTION

Traditional methods for detecting biological compounds in vivo and in vitro rely on the use of radioactive markers. For example, these methods commonly use radiolabeled probes such as nucleic acids labeled with $^{32}P$ or $^{35}S$ and proteins labeled with $^{35}S$ or $^{125}I$ to detect biological molecules. These labels are effective because of the high degree of sensitivity for the detection of radioactivity. However, many basic difficulties exist with the use of radioisotopes. Such problems include the need for specially trained personnel, general safety issues when working with radioactivity, inherently short half-lives with many commonly used isotopes, and disposal problems due to full landfills and governmental regulations. As a result, current efforts have shifted to utilizing non-radioactive methods of detecting biological compounds. These methods often consist of the use of fluorescent molecules as tags (e.g. fluorescein, ethidium, methyl coumarin, rhodamine, and Texas red), or the use of chemiluminescence as a method of detection. Presently however, problems still exist when using these fluorescent and chemiluminescent markers. These problems include photobleaching, spectral separation, low fluorescence intensity, short half-lives, broad spectral linewidths, and non-gaussian asymmetric emission spectra having long tails.

Fluorescence is the emission of light resulting from the absorption of radiation at one wavelength (excitation) followed by nearly immediate reradiation usually at a different wavelength (emission). Fluorescent dyes are frequently used as tags in biological systems. For example, compounds such as ethidium bromide, propidium iodide, Hoechst dyes (e.g., benzoxanthene yellow and bixbenzimide ((2'-[4-hydroxyphenyl]-5-[4-methyl-1-piperazinyl]-2,5'-bi-1H-benzimidazol) and (2'-[4-ethoxyphenyl]-5-[4-methyl-1-piperazinyl]-2,5'-bi-1H-benzimidazol)), and DAPI (4,6-diamidino-2-phenylindole) interact with DNA and fluoresce to visualize DNA. Other biological components can be visualized by fluorescence using techniques such as immunofluorescence which utilizes antibodies labeled with a fluorescent tag and directed at a particular cellular target. For example, monoclonal or polyclonal antibodies tagged with fluorescein or rhodamine can be directed to a desired cellular target and observed by fluorescence microscopy. An alternate method uses secondary antibodies that are tagged with a fluorescent marker and directed to the primary antibodies to visualize the target.

Another application of fluorescent markers to detect biological compounds is fluorescence in situ hybridization (FISH). Swiger et al. (1996) *Environ. Mol. Mutagen.* 27:245–254; Raap (1998) *Mut. Res.* 400:287–298; Nath et al. (1997) *Biotechnic. Histol.* 73:6–22. This method involves the fluorescent tagging of an oligonucleotide probe to detect a specific complementary DNA or RNA sequence. An alternative approach is to use an oligonucleotide probe conjugated with an antigen such as biotin or digoxygenin and a fluorescently tagged antibody directed toward that antigen to visualize the hybridization of the probe to its DNA target. FISH is a powerful tool for the chromosomal localization of genes whose sequences are partially or fully known. Other applications of FISH include in situ localization of mRNA in tissues samples and localization of non-genetic DNA sequences such as telomeres. A variety of FISH formats are known in the art. Dewald et al. (1993) *Bone Marrow Transplantation* 12:149–154; Ward et al. (1993) *Am. J. Hum. Genet.* 52:854–865; Jalal et al. (1998) *Mayo Clin. Proc.* 73:132–137; Zahed et al. (1992) *Prenat. Diagn.* 12:483–493; Kitadai et al. (1995) *Clin. Cancer Res.* 1:1095–1102; Neuhaus et al. (1999) *Human Pathol.* 30:81–86; Hack et al., eds., (1980) *Association of Cytogenetic Technologists Cytogenetics Laboratory Manual.* (Association of Cytogenetic Technologists, San Francisco, Calif.); Buno et al. (1998) *Blood* 92:2315–2321; Patterson et al. (1993) *Science* 260:976–979; Patterson et al. (1998) *Cytometry* 31:265–274; Borzi et al. (1996) *J. Immunol. Meth.* 193:167–176; Wachtel et al. (1998) *Prenat. Diagn.* 18:455–463; Bianchi (1998) *J. Perinat. Med.* 26:175–185; and Munne (1998) *Mol. Hum. Reprod.* 4:863–870.

Fluorescent dyes also have applications in non-cellular biological systems. For example, the advent of fluorescently-labeled nucleotides has facilitated the development of new methods of high-throughput DNA sequencing and DNA fragment analysis_(ABI system; Perkin-Elmer, Norwalk, Conn.). DNA sequencing reactions that once occupied four lanes on DNA sequencing gels can now be analyzed simultaneously in one lane. Briefly, four reactions are performed to determine the positions of the four nucleotide bases in a DNA sequence. The DNA products of the four reactions are resolved by size using polyacrylamide gel electrophoresis. With singly radiolabeled ($^{32}P$ or $^{35}S$) DNA, each reaction is loaded into an individual lane. The resolved products result in a pattern of bands that indicate the identity of a base at each nucleotide position. This pattern across four lanes can be read like a simple code corresponding to the nucleotide base sequence of the DNA template. With fluorescent dideoxynucleotides, samples containing all four reactions can be loaded into a single lane. Resolution of the products is possible because each sample is marked with a different colored fluorescent dideoxynucleotide. For example, the adenine sequencing reaction can be marked with a green fluorescent tag and the other three reactions marked with different fluorescent colors. When all four reactions are analyzed in one lane on a DNA sequencing gel, the result is a ladder of bands consisting of four different colors. Each fluorescent color corresponds to the identity of a nucleotide base and can be easily analyzed by automated systems.

There are chemical and physical limitations to the use of organic fluorescent dyes. One of these limitations is the variation of excitation wavelengths of different colored dyes. As a result, simultaneously using two or more fluorescent tags with different excitation wavelengths requires multiple excitation light sources. This requirement thus adds to the cost and complexity of methods utilizing multiple fluorescent dyes.

Another drawback when using organic dyes is the deterioration of fluorescence intensity upon prolonged exposure to excitation light. This fading is called photobleaching and is dependent on the intensity of the excitation light and the duration of the illumination. In addition, conversion of the dye into a nonfluorescent species is irreversible. Furthermore, the degradation products of dyes are organic compounds which may interfere with biological processes being examined.

Another drawback of organic dyes is the spectral overlap that exists from one dye to another. This is due in part to the relatively wide emission spectra of organic dyes and the overlap of the spectra near the tailing region. Few low molecular weight dyes have a combination of a large Stokes shift, which is defined as the separation of the absorption and emission maxima, and high fluorescence output. In addition, low molecular weight dyes may be impractical for some applications because they do not provide a bright enough fluorescent signal. The ideal fluorescent label should fulfill many requirements. Among the desired qualities are the following: (i) high fluorescent intensity (for detection in small quantities), (ii) a separation of at least 50 nm between the absorption and fluorescing frequencies, (iii) solubility in water, (iv) ability to be readily linked to other molecules, (v) stability towards harsh conditions and high temperatures, (vi) a symmetric, nearly gaussian emission lineshape for easy deconvolution of multiple colors, and (vii) compatibility with automated analysis. At present, none of the conventional fluorescent labels satisfies all these requirements. Furthermore, the differences in the chemical properties of standard organic fluorescent dyes make multiple, parallel assays quite impractical since different chemical reactions may be involved for each dye used in the variety of applications of fluorescent labels.

Thus, there is a need in the art for a fluorescent label that satisfies the above-described criteria for use in biological assay systems

SUMMARY OF THE INVENTION

The present invention provides a composition that can provide information about a biological state or event. The composition by way of example can detect the presence or amounts of a biological moiety, e.g., a biological target analyte; the structure, composition, and conformation of a biological moiety, e.g., a biological molecule or a portion or fragment thereof; the localization of a biological moiety, e.g., a biological target analyte in an environment; interactions of biological moieties, e.g., a biological molecule or a portion or fragment thereof; alterations in structures of biological compounds, e.g., a biological molecule or a portion or fragment thereof; and/or alterations in biological processes.

The composition is comprised of a fluorescent semiconductor nanocrystal (also know as a Quantum Dot™ particle) having a characteristic spectral emission, which is tunable to a desired energy by selection of the particle size, size distribution and composition of the semiconductor nanocrystal. The composition further comprises a compound associated with the semiconductor nanocrystal that has an affinity for a biological target. The composition interacts or associates with a biological target due to the affinity of the compound with the target. Location and nature of the association can be detected by monitoring the emission of the semiconductor nanocrystal.

In operation, the composition is introduced into an environment containing a biological target and the composition associates with the target. The composition:target complex may be spectroscopically view or otherwise detected, for example, by irradiation of the complex with an excitation light source. The semiconductor nanocrystal emits a characteristic emission spectrum which can be observed and measured, for example, spectroscopically.

As an advantage of the composition of the present invention, the emission spectra of a population of semiconductor nanocrystals have linewidths as narrow as 25–30 nm, depending on the size distribution heterogeneity of the sample population, and lineshapes that are symmetric, gaussian or nearly gaussian with an absence of a tailing region. The combination of tunability, narrow linewidths, and symmetric emission spectra without a tailing region provides for high resolution of multiply-sized nanocrystals, e.g., populations of monodisperse semiconductor nanocrystals having multiple distinct size distributions, within a system and enables researchers to examine simultaneously a variety of biological moieties, e.g., target analytes, tagged with nanocrystals.

In addition, the range of excitation wavelengths of the nanocrystals is broad and can be higher in energy than the emission wavelengths of all available semiconductor nanocrystals. Consequently, this allows the simultaneous excitation of all populations of semiconductor nanocrystals in a system having distinct emission spectra with a single light source, usually in the ultraviolet or blue region of the spectrum. Semiconductor nanocrystals are also more robust than conventional organic fluorescent dyes and are more resistant to photobleaching than the organic dyes. The robustness of the nanocrystal also alleviates the problem of contamination of the degradation products of the organic dyes in the system being examined. Therefore, the present invention provides uniquely valuable tags for detection of biological molecules and the interactions they undergo.

In one preferred embodiment, the composition comprises semiconductor nanocrystals associated with molecules that can physically interact with biological compounds. Without limiting the scope of the invention, molecules include ones that can bind to proteins, nucleic acids, cells, subcellular organelles, and other biological molecules. The compound used in the composition of the present invention preferably has an affinity for a biological target. In some preferred embodiments, the compound has a specific affinity for a biological target. The affinity may be based upon any inherent properties of the compound, such as without limitation, van der Waals attraction, hydrophilic attractions, ionic, covalent, electrostatic or magnetic attraction of the compound to a biological target. As used herein, "biological target" is meant any moiety, compound, cellular or subcellular component which is associated with biological functions. The biological target includes without limitation proteins, nucleic acids, cells, subcellular organelles and other biological moieties.

In another preferred embodiment, the composition comprises semiconductor nanocrystals associated with proteins. Without limiting the scope of the invention, the proteins may be antibodies that are directed towards specific antigens, for example, biological antigens such as other proteins, nucleic acids, subcellular organelles, and small molecules that are conjugated to biological compounds. The proteins may also be proteins that interact specifically or non-specifically with other biological compounds.

In another preferred embodiment, the composition comprises semiconductor nanocrystals associated with nucleic acids. Without limiting the scope of the invention, the nucleic acids may be oligonucleotides or deoxyribooligonucleotides that hybridize to nucleic acid polymers in vivo or in vitro. The nucleic acids may also be nucleotides, deoxynucleotides, dideoxynucleotides, or derivatives and combinations thereof that are used for the synthesis of DNA or RNA.

In another aspect of the invention, a method of detecting biological compounds using semiconductor nanocrystals is provided.

These and other embodiments of the present invention will readily occur to those of ordinary skill in the art in view of the disclosure herein.

DETAILED DESCRIPTION OF THE INVENTION

Definitions and nomenclature

Figure 1:
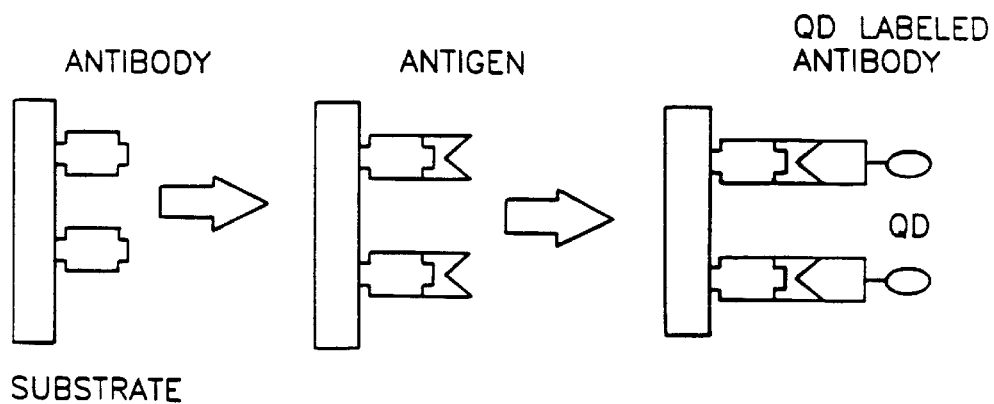
FIG. 1 is a pictorial depiction of the single-sized semiconductor nanocrystal preparation labeled immunoassay.

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a nanocrystal" includes more than one nanocrystal, reference to "a target analyte" includes more than one such analyte, and the like.

In this specification and in the claims which follow, reference will be made to a number of terms which shall be defined to have the following meanings:

"Quantum dot™ particles" are a semiconductor nanocrystal with size-dependent optical and electronic properties. In particular, the band gap energy of a semiconductor nanocrystal varies with the diameter of the crystal.

"Semiconductor nanocrystal" includes, for example, inorganic crystallites between about 1 nm and about 1000 nm in diameter, preferably between about 2 nm and about 50 um, more preferably about 5 nm to about 20 nm (such as about 6, 7, 8, 9, 10, 11, 12, 13, 14, 15, 16, 17, 18, 19, or 20 nm) that includes a "core" of one or more first semiconductor materials, and which may be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap greater than the bandgap of the core material and can be chosen so to have an atomic spacing close to that of the "core" substrate. The core and/or the shell can be a semiconductor material including, but not limited to, those of the group II–VI (ZnS, ZnSe, ZnTe, CdS, CdSe, CdTe, HgS, HgSe, HgTe, MgTe and the like) and III–V (GaN, GaP, GaAs, GaSb, InN, InP, InAs, InSb, AlAs, AlP, AlSb, AlS, and the like) and IV (Ge, Si, Pb and the like) materials, and an alloy thereof, or a mixture thereof.

A semiconductor nanocrystal is, optionally, surrounded by a "coat" of an organic capping agent. The organic capping agent may be any number of materials, but has an affinity for the semiconductor nanocrystal surface. In general, the capping agent can be an isolated organic molecule, a polymer (or a monomer for a polymerization reaction), an inorganic complex, and an extended crystalline structure. The coat is used to convey solubility, e.g., the ability to disperse a coated semiconductor nanocrystal homogeneously into a chosen solvent, functionality, binding properties, or the like. In addition, the coat can be used to tailor the optical properties of the semiconductor nanocrystal.

As used herein, the term "binding pair" refers first and second molecules that specifically bind to each other. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically non-covalent. The terms "affinity molecule" and "target analyte" are used herein to refer to first and second members of a binding pair, respectively.

Exemplary binding pairs include any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-strepavidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like.

"Semiconductor nanocrystal conjugate" or "nanocrystal conjugate" includes, for example, a semiconductor nanocrystal linked, through the coat, to a member of a "binding pair" that will selectively bind to a detectable substance present in a sample, e.g., biological sample as defined herein. The first member of the binding pair linked to the semiconductor nanocrystal can comprise any molecule, or portion of any molecule, that is capable of being linked to a semiconductor nanocrystal and that, when so linked, is capable of recognizing specifically the second member of the binding pair.

"Monodisperse particles" include a population of particles wherein at least 60% of the particles in the population fall within a specified particle size range. A population of monodispersed particles deviate less than 10% rms (root-mean-square) in diameter and preferably less than 5% rms.

"Quantum yield" yield is defined as the ratio of photons emitted to that absorbed.

The terms "polynucleotide," "oligonucleotide," "nucleic acid" and "nucleic acid molecule" as used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oregon, as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

The terms "polynucleotide analyte" and "nucleic acid analyte" are used interchangeably and include a single- or double-stranded nucleic acid molecule that contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, or the like.

As used herein, the term "target nucleic acid region" or "target nucleotide sequence" includes a probe-hybridizing region contained within the target molecule. The term "target nucleic acid sequence" includes a sequence with which a probe will form a stable hybrid under desired conditions.

As used herein, the term "nucleic acid probe" includes reference to a structure comprised of a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include posttranslational modifications of the polypeptide, for example, glycosylations, acetylations, phosphorylations and the like. In addition, protein fragments, analogs, mutated or variant proteins, fusion proteins and the like are included within the meaning of polypeptide.

The term "alkyl" as used herein includes reference to a branched or unbranched saturated hydrocarbon group of 1 to 100 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" includes an alkyl group of 1 to 20 carbon atoms, preferably 6 to 20 carbon atoms.

The term "alkylene" as used herein includes reference to a di-functional saturated branched or unbranched hydrocarbon chain containing from 1 to 100 carbon atoms, and includes, for example, methylene ($—CH_2—$), ethylene ($—CH_2—CH_2—$), propylene ($—CH_2—CH_2—CH_2—$), 2-methylpropylene ($—CH_2—CH(CH_3)—CH_2—$), hexylene ($—(CH_2)_6—$), and the like. "Lower alkylene" includes an alkylene group of 1 to 20, more preferably 6 to 20, carbon atoms.

The term "alkenyl" as used herein includes reference to a branched or unbranched hydrocarbon group of 2 to 100 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. The term "lower alkenyl" includes an alkenyl group of 2 to 20 carbon atoms, preferably 6 to 20 carbon atoms, containing one C=C bond.

The term "alkenylene" includes reference to a difunctional branched or unbranched hydrocarbon chain containing from 2 to 100 carbon atoms and at least one carbon-carbon double bond. "Lower alkenylene" includes an alkenylene group of 2 to 20, more preferably 6 to 20, carbon atoms, containing one carbon-carbon double bond.

The term "alkynyl" as used herein includes reference to a branched or unbranched hydrocarbon group of 2 to 100 carbon atoms containing at least one C≡C bond, such as ethynyl, n-propynyl, isopropynyl, n-butynyl, isobutynyl, t-butynyl, octynyl, decynyl and the like. Preferred alkynyl groups herein contain 6 to 20 carbon atoms. The term "lower alkynyl" includes an alkynyl group of 2 to 10 carbon atoms, and one C≡C bond.

The term "alkynylene" includes reference to a difunctional branched or unbranched hydrocarbon chain containing from 2 to 100 carbon atoms and at least one carbon-carbon triple bond. "Lower alkynylene" includes an alkynylene group of 2 to 10 carbon atoms, containing one —C≡C— bond.

Optionally, an alkyl, alkylene, alkenyl, alkenylene, alkynyl or alkynyl chain can contain 1 to 6 linkages selected from the group consisting of —O—, —S— and —NR— wherein R is hydrogen, lower alkyl or lower alkenyl.

The terms "heteroalkyl," "heteroalkylene," "heteroalkenyl," "heteroalkenylene," "heteroalkynyl" and "heteroalkynylene" include reference to alkyl, alkylene, alkenyl, alkenylene, alkynyl and alkynylene groups, respectively, in which one or more of the carbon atoms have been replaced with, e.g., nitrogen, sulfur or oxygen atoms.

"Alkoxy" includes reference to the group —O—R, wherein R is an alkyl radical as defined above. Examples of an alkoxy radical include, but are not limited to, methoxy, ethoxy, isopropoxy and the like.

"Alkylamino" includes reference to a radical —NHR, wherein R is an alkyl radical as defined above. Examples of alkylamino radicals include, but are not limited to, methylamino, (lethylethyl)amino, and the like.

"Alkylthio" includes reference to a radical —SR where R is an alkyl radical as defined above. Examples of alkylthio radicals include, but are not limited to, methylthio, butylthio, and the like.

"Dialkylamino" includes reference to a radical —NR'R", wherein R' and R" are each independently alkyl radicals as defined above. Examples of dialkylamino radicals include, but are not limited to, dimethylamino, methylethylamino, diethylamino, di(1 methylethyl)amino, and the like.

"Hydroxyalkyl" includes reference to an alkyl radical as defined above, substituted with one or more hydroxy groups. Examples of hydroxyalkyl radicals include, but are not limited to, hydroxymethyl, 2-hydroxyethyl, 2hydroxypropyl, 3hydroxypropyl, 2-hydroxybutyl, 3-hydroxybutyl, 4-hydroxybutyl, 2,3dihydroxypropyl, 1-(hydroxymethyl)-2-hydroxyethyl, 2,3-dihydroxybutyl, 3,4dihydroxybutyl, and 2-(hydroxymethyl)-3-hydroxypropyl, and the like.

The term "acyl" as used herein includes reference to an alkyl group bound through a —(CO)— linkage. The term "lower acyl" includes an acyl group in which the alkyl group bound through the carbonyl linkage is a lower alkyl group.

The term "sugar moiety" includes reference to monosaccharides, disaccharides, polysaccharides, and the like. The term "sugar" includes those moieties which have been modified, e.g., wherein one or more of the hydroxyl groups are replaced with halogen, alkoxy moieties, aliphatic groups, or are functionalized as ethers, amines, or the like. Examples of modified sugars include: those which contain a lower alkoxy group in place of a hydroxyl moiety, i.e., (- or (-glycosides such as methyl (-D-glucopyranoside, methyl (-D-glucopyranoside, and the like; those which have been reacted with amines, i.e., N-glycosylamines or N-glycosides such as N-((-D-glucopyranosyl)methylamine; those containing acylated hydroxyl groups, typically from 1 to 5 lower acyl groups; those containing one or more carboxylic acid groups, e.g., D-gluconic acid or the like; and those containing free amine groups such as D-glucosamine, D-galactosamine, N-acetyl-D-glucosamine or the like. Examples of preferred saccharides are glucose, galactose, fructose, ribose, mannose, arabinose, xylose. Examples of polysaccharides is dextran and cellulose.

"Aryl" includes reference to a monovalent aromatic hydrocarbon radical consisting of one or more fused rings in which at least one ring is aromatic in nature, which can optionally be substituted with one or more of the following substituents: hydroxy, cyano, alkyl, alkoxy, thioalkyl, halo, haloalkyl, hydroxyalkyl, nitro, amino, alkylamino, and dialkylamino, unless otherwise indicated.

"Heteroaryl" includes reference to a monovalent aromatic carbocyclic radical having one or more rings incorporating one, two or three heteroatoms within the ring (chosen from nitrogen, oxygen, or sulfur) which can optionally be substituted with one or more of the following substituents: hydroxy, cyano, alkyl, alkoxy, thioalkyl, halo, haloalkyl, hydroxyalkyl, nitro, amino, and alkylamino and dialkylamino, unless otherwise indicated. "Cycloalkyl" includes reference to a monovalent saturated carbocyclic radical consisting of one or more rings, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

"Cycloalkenyl" includes reference to a monovalent unsaturated carbocyclic radical consisting of one or more rings and containing one or more carbon-carbon double bonds, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

"Cycloalkynyl" includes reference to a monovalent unsaturated carbocyclic radical consisting of one or more rings and containing one or more carbon-carbon triple bonds, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

"Heterocyclic" includes reference to a monovalent saturated carbocyclic radical, consisting of one or more rings, incorporating one, two or three heteroatoms (chosen from nitrogen, oxygen or sulfur), which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

The term "crown ether" includes reference to a saturated unbranched heterocyclic molecule, mono-, di-, tri-valent or higher (e.g., 4, 5, 6, 7, or 8) multivalent radical, . Crown ethers are typically referred to as "x crown y" or "xCy"

wherein x represents the total number of atoms in the molecule and y represents the number of heteroatoms in the molecule. Thus, for example, 12 crown 4 is a crown ether containing 12 atoms, 4 of which are heteroatoms and 18C6 is a crown ether containing 18 atoms, 6 of which are heteroatoms. Preferred heteroatoms are O, S and N, and in any particular crown ether the heteroatoms can be the same or different. A "heterocrown ether" is a crown ether in which the heteroatoms are different. Preferred crown ethers are six- to thirty-membered crown or heterocrown ethers, more preferred are 8C4, 9C3, 12C4, 15C5, 18C6 and 20C8, and even more preferred are 12C4 and 18C6.

As used herein, a "biological sample" includes reference to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

A "small molecule" is defined as including an organic compound either synthesized in the laboratory or found in nature. Typically, a small molecule is characterized in that it contains several carbon-carbon bonds, and has a molecular weight of less than 1500 grams/Mol.

A "biological state" is defined as including the quantitative and qualitative presence of a biological moiety; the structure, composition, and conformation of a biological moiety; and the localization of a biological moiety in an environment.

A "biological event" is defined as including an interaction of biological moieties, a biological process, an alteration in the structures of a biological compounder an alteration in a biological process.

The term "multiplexing" is used herein to include conducting an assay or other analytical method in which multiple analytes or biological states can be detected simultaneously by using more than one detectable label, each of which emits at a distinct wavelength and, preferably, each of which is linked to one of a plurality of first members of binding pairs each of which first members is capable of binding to a distinct corresponding second member of the binding pair. A multiplexed method using semiconductor nanocrystals having distinct emission spectra can be used to detect simultaneously in the range of 2 and 10,000 analytes, biological compounds or biological states, preferably in the range of 10 and 100, and more preferably in the range of up to 10 to 20, e.g., 2, 3, 4, 5, 6, 7, 8, 9, 10, 11, 12, 13, 14, 15, 16, 17, 18, 19, or 20, analytes or biological states. Multiplexing also includes assays or methods in which the combination of more than one semiconductor nanocrystal having distinct emission spectra can be used to detect a single analyte.

"Optional" or "optionally" means that the subsequently described event or circumstance may or may not occur, and that the description includes instances where said event or circumstance occurs and instances where it does not. For example, the phrase "optionally washed" means that a washing step may or may not occur and that the description of the method includes both proceeding with or without a wash step, the phrase "optionally substituted alkylene" means that an alkylene moiety may or may not be substituted and that the description includes both unsubstituted alkylene and alkylene where there is substitution, and the like.

The present invention provides a composition comprising semiconductor nanocrystals (also referred to in this application as semiconductor nanocrystals) as fluorescent tags associated with a reagent or molecule wherein the composition can detect the presence or amount of a biological molecule, detect biological interactions, detect biological processes, detect alterations in biological processes, or detect alterations in the structure of a biological compound.

Semiconductor nanocrystals demonstrate quantum confinement effects in their luminescent properties. When semiconductor nanocrystals are illuminated with a primary energy source, a secondary emission of energy occurs of a frequency that corresponds to the band gap of the semiconductor material used in the semiconductor nanocrystal. In quantum confined particles, the band gap is a function of the size of the nanocrystal.

Furthermore, semiconductor nanocrystals or nanoparticles constitute a new class of luminescent material intermediate between molecular and bulk forms of matter. A population of such nanocrystals can be simultaneously excited using a single wavelength of light and the detectable luminescence can be engineered to occur at a plurality of wavelengths. The luminescent emission is related to the size, the size distribution and the composition of the constituent semiconductor nanocrystals of the population. Furthermore, the nanoparticles can be made highly luminescent through the use of an inorganic shell material which efficiently encapsulates the surface of the semiconductor nanocrystal core. A "core/shell" semiconductor nanocrystal has a high quantum efficiency and significantly improved photochemical stability. The surface of the core/shell semiconductor nanocrystal can be modified to produce nanocrystals that can be coupled to a variety of biological molecules by techniques described in, for example, Bruchez et. al. (1998) Science 281:2013–2016., Chan et. al. (1998) Science 281:2016–2018, and in Bruchez "Luminescent Semiconductor Nanocrystals: Intermittency Properties and Use as Fluorescent Biological Labels" (1998) Doctoral dissertation, University of California, Berkeley.

Many semiconductors that are constructed of elements from groups II–VI, III–V and IV of the periodic table have been prepared as quantum sized particles, exhibit quantum confinement effects in their physical properties, and can be used in the composition of the invention. Exemplary materials suitable for use as semiconductor nanocrystal cores include, but are not limited to, CdS, CdSe, CdTe, ZnS, ZnSe, ZnTe, MgTe, GaAs, GaP, GaSb,GaN, HgS, HgSe, HgTe, InAs, InP, InSb, InN, AlAs, AlP, AlSb, AlS, PbS, PbSe,Ge, Si, an alloy thereof, or a mixture thereof, including ternary and quaternary mixtures. Optionally, the core is overcoated with a shell material comprising ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, an alloy thereof, or a mixture thereof. Preferably, the band gap energy of the overcoating is greater than that of the core.

The semiconductor nanocrystals are characterized by their uniform nanometer size. By "nanometer" size, it is meant less than about 150 Angstroms (Å), and preferably in the range of 12–150 Å. The nanocrystals also are substantially monodisperse within the broad nanometer range given above. By "monodisperse," as that term is used herein, it is meant a colloidal system in which the suspended particles have substantially identical size and shape. For the purpose of the present invention, mondisperse particles mean that at least 60% of the particles fall within a specified particle size range. Monodisperse particles deviate less than 10% rms in diameter, and preferably less than 5% rms.

The narrow size distribution of the semiconductor nanocrystals allows the possibility of light emission in narrow spectral widths. Monodisperse semiconductor nanocrystals have been described in detail in Murray et al. (J. Am. Chem. Soc., 115:8706 (1993)); in the thesis of Christopher Murray, "Synthesis and Characterization of II–VI Quantum Dots and Their Assembly into 3-D Quantum Dot Superlattices", Massachusetts Institute of Technology, September, 1995; and in U.S. patent application Ser. No. 08/969,302 entitled "Highly Luminescent Color-selective Materials" which are hereby incorporated in their entireties by reference.

The fluorescence of semiconductor nanocrystals results from confinement of electronic excitations to the physical dimensions of the nanocrystals. In contrast to the bulk semiconductor material from which these nanocrystals are synthesized, these semiconductor nanocrystals have discrete optical transitions, which are tunable with size (see, U.S. patent application Ser. No. 08/969,302, entitled "Highly Luminescent Color-Selective Materials," by Bawendi et al., filed Nov. 13, 1997). Current technology allows good control of their sizes (between 12 to 150 Å; standard deviations approximately 5%), and thus, enables construction of semiconductor nanocrystals that emit light at a desired wavelength throughout the UV-visible-IR spectrum with a quantum yield ranging from 30–50% at room temperature in organic solvents and 10–30% at room temperature in water.

Techniques for producing semiconductor nanocrystals that fluoresce in a narrow spectral distribution of a selected color are discussed further below and in Dabbousi et al. (1997) J. Phys. Chem. B 101:9463–9475 and in copending U.S. patent application Ser. No. 08/969,302, supra. However, other techniques for producing semiconductor nanocrystals are also encompassed within the scope of the invention.

For example, CdSe nanocrystals can be produced that emit light visible to the human eye, so that in combination with a source of higher energy than the highest energy of the desired color, these nanocrystals can be tailored to produce visible light of any spectral distribution. Semiconductor nanocrystals can also be produced that emit in the ultraviolet and infra red spectral ranges. Examples of ultraviolet- and infra red-emitting nanocrystals are, e.g., CdS, ZnS and ZnSe, and InAs, CdTe and MgTe, respectively.

The color of light produced by a particular size, size distribution and/or composition of a semiconductor nanocrystal may be readily calculated or measured by methods which will be apparent to those skilled in the art. As an example of these measurement techniques, the band gaps for nanocrystals of CdSe of sizes ranging from 12 Å to 115 Å are given in Murray et al. (1993) J. Am. Chem. Soc. 115:8706. These techniques allow ready calculation of an appropriate size, size distribution and/or composition of semiconductor nanocrystals and choice of excitation light source to produce a nanocrystal capable of emitting light device of any desired wavelength.

A number of methods of producing semiconductor nanocrystals are known in the art. Any method of producing nanocrystals that will fluoresce with a desired spectrum may be used in the practice of the invention. Preferably, the methods described in Dabbousi et al., supra, and U.S. application Ser. No. 08/969,302, supra, can be used to produce semiconductor nanocrystals useful in compositions and methods as disclosed and claimed herein.

In addition, Dabbousi et al., supra, discloses a method that can be used for overcoating nanocrystals composed of CdS, CdSe, or CdTe with ZnS, ZnSe, or mixtures thereof. Before overcoating, a nanocrystal core is prepared by a method described in Murray et al., supra, that yields a substantially monodisperse size distribution. An overcoat of a controlled thickness can then be applied by controlling the duration and temperature of growth of the coating layer as described in Dabbousi et al. The monodispersity of the core nanocrystal results in monochromatic emission. The overcoated core nanocrystal has an improved quantum efficiency and emits more light than a bare core nanocrystal.

The above method can be used to prepare separate populations of semiconductor nanocrystals, wherein each population exhibits a different characteristic photoluminescence spectrum. Each of a plurality of populations of semiconductor nanocrystals can be conjugated to distinct first members of binding pairs for use in a multiplexed assay or analytical method in which each of a plurality of corresponding second members of the binding pairs can be detected simultenously.

The present invention provides a composition comprising semiconductor nanocrystals associated with a reagent or molecule or affinity molecule such that the composition can detect the presence and/or amounts of biological compounds, detect interactions in biological systems, detect biological processes, detect alterations in biological processes, or detect alterations in the structure of biological compounds. Without limitation to the present invention, these reagents or molecule or nanocrystal conjugate or affinity molecule include any molecule or molecular complex that can interact with a biological target, molecules or molecular complexes or nanocrystal conjugates that can associate with biological targets to detect biological processes, or reactions, and molecules or molecular complexes or conjugates that can alter biological molecules or processes. Preferably, the molecules or molecular complexes or conjugates physically interact with a biological compounds. Preferably, the interactions are specific. The interactions can be, but are not limited to, covalent, noncovalent, hydrophobic, hydrophilic, electrostatic, van der Waals, or magnetic. Preferably, these molecules are small molecules, proteins, or nucleic acids or combinations thereof.

Semiconductor nanocrystals are capable of fluorescence when excited by light. Currently, detection of biological compounds by photoluminescence utilizes fluorescent organic dyes and chemiluminescent compounds. The use of nanocrystals as fluorescent markers in biological systems provides advantages over existing fluorescent organic dyes. Many of these advantages relate to the spectral properties of nanocrystals. For example without limiting the scope of the present invention, the ability to control the size of nanocrystals enables one to construct nanocrystals with fluorescent emissions at any wavelength in the UV-visible-IR region. Therefore, the colors (emissions) of nanocrystals are tunable to any desired spectral wavelength. Furthermore, the emission spectra of monodisperse nanocrystals have linewidths as narrow as 25–30 nm. The linewidths are dependent on the size heterogeneity, i.e., monodispersity of the population of nanocrystals in each preparation. Single semiconductor nanocrystals or monodisperse populations of semiconductor nanocrystals have been observed to have full width at half max ("FWHM") of 12–15 nm. In addition, nanocrystals with larger FWHM in the range of 40–60 nm can be readily made and have the same physical characteristics, such as emission wavelength tunability and excitation in the UV-blue, preferably in the blue region of the spectrum, as nanocrystals with narrower FWHM.

The narrow spectral linewidths and nearly gaussian symmetrical lineshapes lacking a tailing region observed for the emission spectra of nanocrystals combined with the tunability of the emission wavelengths of nanocrystals allows high spectral resolution in a system with multiple nanocrystals. In theory, but without limitation, up to 10–20 or more different-sized nanocrystals or different size distributions of monodisperse populations of nanocrystals from different preparations of nanocrystals, with each sample having a different emission spectrum, can be used simultaneously in one system, i.e., multiplexing, with the overlapping spectra easily resolved using techniques well known in the art, e.g., optically with or without the use of deconvolution software.

Another advantage to the use of nanocrystals as fluorescent markers over existing organic fluorescent dyes is that only a single light source (usually in the UV-blue, and preferably in the blue region of the spectrum) is needed to excite all nanocrystals in a system. The light source is one capable of emitting light having an energy spectrum that includes light of higher energies than the light energy emitted by the nanocrystals, e.g., commonly, but not necessarily, in the UV-blue, and preferably in the blue region of the spectrum. By contrast, organic dyes with different emission wavelengths usually have different excitation wavelengths. Thus, multiple light sources or a single light source with adaptable light-filters are needed for systems that utilize organic dyes with different excitation wavelength. Since, generally, all nanocrystals of the present invention can be excited by light in the UV-blue region of the spectrum (preferably the blue visible region), a single light source can be used. This minimizes the technical complexity needed to provide an excitation light source. In addition, by using blue light, the source radiation will not interfere with any of the fluorescence measurements taken in the visible or infrared region of the light spectrum, and also will not damage biological molecules. For example, UV light can cause dimerization in DNA molecules.

Another advantage of the use of nanocrystals over organic fluorescent dyes that are currently available is the robust nature of the nanocrystals due to their crystalline inorganic structure and their protective overcoating layer. These nanocrystals are more resistant to photobleaching than what is observed for organic dyes. Also, since nanocrystals described in the application are composed of similar materials and are protected by the same organic capping groups, chemical uniformity of nanocrystals allows the extrapolation of a protocol developed to attach one particular size of nanocrystals to a molecule to nanocrystals of all sizes within that class of nanocrystals. Such uniformity should be valuable in extending conventional assaying techniques to include parallel detection schemes. Therefore, the present invention provides a series of fluorescent probes, which span the spectrum from the UV to the IR, and also can have substantially identical chemical properties.

Because detection of biological compounds is most preferably carried out in aqueous media, a preferred embodiment of the present invention utilizes semiconductor nanocrystals that are solubilized in water. Semiconductor nanocrystals described by Bawendi et al. (J. Am. Chem. Soc., 115:8706, 1993) are soluble or dispersible only in organic solvents, such as hexane or pyridine. It is preferred that the nanocrystals are water-soluble and associated with molecules capable of interacting with biological compounds. However, alternative methods of associating molecules to nanocrystals may be used to obtain similar results. Bawendi et al. have described methods for construction of water-soluble nanocrystals suitable for biological systems (commonly assigned U.S. patent application Ser. No. 09/156,863 by Bawendi et al., entitled "Water-Soluble Luminescent Nanocrystals," incorporated herein by reference and filed on Sep. 18, 1998).

A water-solubilizing layer is found at the outer surface of the overcoating layer. The outer layer includes a water-solubilizing compound having at least one linking group for attachment of the compound to the overcoating layer and at least one hydrophilic group, optionally the hydrophilic group is spaced apart from the linking group by a hydrophobic region, or spacer, sufficient to prevent electron charge transfer across the hydrophobic region. The affinity for the nanocrystal surface promotes coordination of the linking moiety to the semiconductor nanocrystal outer surface and the moiety with affinity for the aqueous medium stabilizes the semiconductor nanocrystal suspension.

Without limitation to the scope of the present invention, the water-solublizing compound may have the structural formula (I)

and salts thereof, where X is S, N, P or O=P; n (6; and z and y are selected to satisfy the valence requirements of X. Exemplary compound for use in the invention may have the structural formula (II)

or structural formula (III)

where X, X' and X" are the same or different and are selected from the group of S, N, P or O=P; Y is a hydrophilic moiety; and Z is a hydrophobic region having a backbone of at least six atoms. X, X' and X" may include other substituents in order to satisfy the valence requirements, such as for example, amines, thiols, phosphines and phosphine oxides, substituted by hydrogen or other organic moieties. In addition, the atoms bridging X, X' and X" are selected to form a 5-membered to 8-membered ring upon coordination to the semiconductor surface. The bridging atoms are typically carbon, but may be other elements, such as oxygen, nitrogen, and sulfur. Y may be any charged or polar group, such as carboxylates, sulfonates, phosphates, polyethylene glycol and other polyols and ammonium salt, e.g., carboxylate (—CO$_2$—), sulfonate (SO$_3$—), hydroxide (—OH), alkoxides, ammonium salts (—NH$_4$+), and phosphate (—PO$_4$—2) and phosphonate (—PO$_3$—2), and the like. Z is typically an alkyl group or alkenyl group, but may also include other atoms, such as carbon and nitrogen. Z may be further modified as described herein to provide attractive interactions with neighboring ligands.

In a particular preferred embodiment, the hydrophilic moiety X also provides a reactive group capable of a reaction to couple the compound to the semiconductor nanocrystal. For example, where the hydrophilic moiety is a —COOH or a —COO group, it may be used to couple a variety of biological compounds to form a corresponding ester, amide, or anhydride. By way of the example only, a carboxylic acid terminated nanocrystals can react with an amino acid to form an amide coupling. The amide may function as the compound having affinity for a biological target.

In another preferred embodiment, the overcoated nanocrystal comprises a water-solublizing outer layer comprising a molecule having structural formula (IV):

wherein:
R$^1$ is selected from the group consisting of heteroalkyl, heteroalkenyl, heteroalkynyl, —OR, —SR, —NHR, —NR'R", —N(O)HR, —N(O)R'R", —PHR, —PR'R", P(NR'R")NR'R",P(O)R'R", P(O)(NR'R")NR'R", —P(O)(OR')OR", P(O)OR, P(O)NR'R", —P(S)(OR')OR", and P(S)OR, wherein R, R' and R" are independently selected from the group consisting of H, a branched or unbranched alkyl, a branched or unbranched alkenyl, a branched or unbranched alkynyl, a branched or unbranched heteroalkyl, a branched or unbranched heteroalkenyl and a branched or unbranched heteroalkynyl, with the proviso that when a is greater than 1 the R$^1$ groups can be the same or different or can be linked to form a six, seven-, eight-, nine- or ten-membered cycloalkyl, cycloalkenyl, heterocyclic, aryl, heteroaryl, or a six- to thirty-membered crown ether or heterocrown ether;

R$^2$ is selected from a bond (i.e., R$^2$ is absent), a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

R$^3$ is selected from a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

R$^4$ is selected from the group consisting of hydrogen, a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, an amine, an ammonium, an alkyl ammonium, a nitrate, a sugar moiety, and a five-, six-, seven-, eight-, nine- or ten-membered cycloalkenyl, cycloalkynyl, heterocyclic, aryl, or heteroaryl;

a is 1, 2, 3 or 4;

b is 0, 1, 2 or 3;

c is 0, 1, 2 or 3; and d is 0, 1, 2 or 3, wherein when d is 2 or 3 the R$^3$ groups can be the same or different or can be linked together to form a five-, six-, seven-, eight-, nine- or ten-membered cycloalkyl, cycloalkenyl, heterocyclic, aryl, or heteroaryl.Although not wishing to be bound by theory, the inventors believe that coordination of the molecule having structural formula (IV) to the overcoated nanocrystal occurs between surface moieties on the nanocrystal and the R$^1$ moiety of the molecule.

Prefereably, R$^1$ is a thiol (e.g., —SH), a phosphine, a phosphine oxide, or an amine (e.g., —NH2, NHR, NRR).

Preferably, R$^2$ contains between 6 and 20 atoms. More preferably, R$^2$ is a linear alkylene, alkenylene, alkynylene, heteroalkylene, heteroalkenylene or heteroalkynylene containing 6, 7, 8, 9, 10, 11, 12, 13, 14, 15, 16, 17, 18, 19 or 20 atoms, or a cycloalkyl or heterocyclic containing 5 or 6 atoms.

Preferably, when b is 1, 2 or 3, R$^3$ contains between 6 and 20 atoms. More preferably, R$^3$ is a linear alkylene, alkenylene, alkynylene, heteroalkylene, heteroalkenylene or heteroalkynylene containing 6, 7, 8, 9, 10, 11, 12, 13, 14, 15, 16, 17, 18, 19 or 20 atoms, or a cycloalkyl or heterocyclic containing 5 or 6 atoms.

Preferably, R$^4$ is a carboxylate (—COO$^-$), a phosphonate (—PO$_3$—). a sulfonate (SO$_3$—) or an ammonium (—N$^+$HRR').

The water-solublizing outer layer can comprise a homogeneous population of molecules having structural formula (I), (II), (III), or (IV), a mixed population of molecules any individual structural formula, i.e., a mixed population of molecules all of which have structural formula (I), (II), (III) or (IV), or a mixed population of molecules which have a combination of two or more of structural formulas (I), (II), (III) and (IV).

In other preferred embodiments, a water-soluble nanocrystal is provided in which the outer layer has been partially substituted by a ligand which terminates in a reactive group. The reactive group is not selected for its hydrophilic properties but rather for its ability to couple with the compound of the invention. Exemplary reactive groups include carboxylic acid groups, thiol groups and amine groups. The ligand can comprise the water-solubilizing compound comprising structural formula (I)

wherein X, z, n and y are as defined above, structural formula (II) or (III)

wherein Y, Z, X, X' and X" are as defined above, or structural formula (IV)

wherein R$^1$, R$^2$, R$^3$, R$^4$, a, b, c, and d are as defined above.

In yet another embodiment of the invention, a water-soluble nanocrystal is provided in which the outer layer is partially substituted by a ligand which comprises the compound of the invention. By way of example only, the compound may include a parent group terminating in a thiol, amine or phosphine or phosphine oxide, which can interact directly with the semiconductor nanocrystal surface.

In one preferred embodiment, the present invention provides a composition comprising a semiconductor nanocrystal that emits light at a tunable wavelength and is associated with a protein. Without limitation to the scope of the invention, the protein can be a peptide or an amino acid or derivatives thereof. Without limiting the scope of the invention since alternative methods may be utilized to achieve the same results, the nanocrystals may be associated with amino acids and peptides through conjugation of an amino acid residue with carboxylic acid groups conjugated with N-hydroxysuccinimide (NHS) on the surface of the nanocrystals. In a preferred embodiment, the semiconductor nanocrystals are water-soluble, and as described in Example 4, creating the water-soluble semiconductor nanocrystals involves covering the surface of the nanocrystals with hydrophilic moieties such as carboxylic acid groups (see, U.S. patent application Ser. No. 09/156,863, entitled "Water-Soluble Fluorescent Nanocrystals", supra). Carboxylic acid groups can be conjugated with N-hydroxysuccinimide (NHS) to activate the carbonyl group for further conjugation with an amino acid residue such as lysine.

As an example without limitation to the present invention, the composition comprises semiconductor nanocrystals associated with a protein that is an antibody. The antibody can be a polyclonal or a monoclonal antibody. Antibodies tagged with nanocrystals as fluorescent markers of one color or of multiple colors can then be used in applications such as immunochemistry and immunocytochemistry.

As another example without limitation to the present invention, the composition comprises nanocrystals conjugated to proteins with desired binding characteristics such as specific binding to another protein (e.g. receptors), binding to ligands (e.g. cAMP, signaling molecules) and binding to nucleic acids (e.g. sequence-specific binding to DNA and/or RNA).

In another preferred embodiment, the present invention provides a composition comprising a semiconductor nanocrystal that emits light at a tunable wavelength and is associated with a molecule or molecular complex that is capable of interacting with a biological compound. As an example without limiting the scope of the invention, nanocrystals can be conjugated to molecules that can interact physically with biological compounds such as cells, proteins, nucleic acids, subcellular organelles and other subcellular components. For example, nanocrystals can be associated with biotin which can bind to the proteins, avidin and streptavidin. Also, nanocrystals can be associated with molecules that bind non-specifically or sequence-specifically to nucleic acids (DNA RNA). As examples without limiting the scope of the invention, such molecules include small molecules that bind to the minor groove of DNA (for reviews, see Geierstanger and Wemmer. Annu Rev Biophys Biomol Struct. 24:463493, 1995; and Baguley. Mol Cell Biochem. 43(3):167181, 1982), small molecules that form adducts with DNA and RNA (e.g. CC-1065, see Henderson and Hurley. J Mol Recognit. 9(2):7587, 1996; aflatoxin, see Garner. Mutat Res. 402(12):6775, 1998; cisplatin, see Leng and Brabec. IARC Sci Publ. 125:339348, 1994), molecules that intercalate between the base pairs of DNA (e.g. methidium, propidium, ethidium, porphyrins, etc. for a review see Bailly, Henichart, Colson, and Houssier. J Mol Recognit. 5(4):155171, 1992), radiomimetic DNA damaging agents such as bleomycin, neocarzinostatin and other enediynes (for a review, see Povirk. Mutat Res. 355(12):7189, 1996), and metal complexes that bind and/or damage nucleic acids through oxidation (e.g. Cu-phenanthroline, see Perrin, Mazumder, and Signan. Prog Nucleic Acid Res Mol Biol. 52:123151, 1996; Ru(II) and Os(II) complexes, see Moucheron, KirscbDe Mesmaeker, and Kelly. J Photochem Photobiol B, 40(2) :91106, 1997; chemical and photochemical probes of DNA, see Nielsen, J Mol Recognit, 3(1):125, 1990).

Molecules and higher order molecular complexes (e.g. polymers, metal complexes) associated with nanocrystals can be naturally occurring or chemically synthesized. Molecules or higher order molecular complexes can be selected to have a desired physical, chemical or biological property. Such properties include, but are not limited to, covalent and noncovalent association with proteins, nucleic acids, signaling molecules, procaryotic or eukaryotic cells, viruses, subcellular organelles and any other biological compounds. Other properties of such molecules, include but are not limited to, the ability to affect a biological process (e.g. cell cycle, blood coagulation, cell death, transcription, translation, signal transduction, DNA damage or cleavage, production of radicals, scavenging radicals, etc.), and the ability to alter the structure of a biological compound (e.g. crosslinking, proteolytic cleavage, radical damage, etc.). In addition, molecules and higher order molecular complexes associated with nanocrystals may have more general physical, chemical or biological properties such as, but not limited to, hydrophobicity, hydrophilicity, magnetism and radioactivity.

In another preferred embodiment, the present invention provides a composition comprising a semiconductor nanocrystal that emits light at a tunable wavelength and is associated with a nucleic acid. The association can be direct or indirect. The nucleic acid can be any ribonucleic acid, deoxyribonucleic acid, dideoxyribonucleic acid, or any derivatives and combinations thereof. The nucleic acid can also be oligonucleotides of any length. The oligonucleotides can be single-stranded, double-stranded, triple-stranded or higher order configurations (e.g. Holliday junctions, circular single-stranded DNA, circular double-stranded DNA, DNA cubes, (see Seeman. Annu Rev Biophys Biomol Struct. 27:225248, 1998)). Among the preferred uses of the present compositions and methods are detecting and/or quantitating nucleic acids as follows: (a) viral nucleic acids; (b) bacterial nucleic acids; and (c) numerous human sequences of interest, e.g. single nucleotide polymorphisms.

Without limiting the scope of the present invention, nanocrystals can be associated with individual nucleotides, deoxynucleotides, dideoxynucleotides or any derivatives and combinations thereof and used in DNA polymerization reactions such as DNA sequencing, reverse transcription of RNA into DNA, and polymerase chain reactions (PCR). Nucleotides also include monophosphate, diphosphate and triphophates and cyclic derivatives such as cyclic adenine monophosphate (cAMP). Other uses of nanocrystals conjugated to nucleic acids included fluorescence in situ hybridization (FISH). In this preferred embodiment, nanocrystals are conjugated to oligonucleotides designed to hybridize to a specific sequence in vivo. Upon hybridization, the fluorescent nanocrystal tags are used to visualize the location of the desired DNA sequence in a cell. For example, the cellular location of a gene whose DNA sequence is partially or completely known can be determined using FISH. Any DNA or RNA whose sequence is partially or completely known can be visually targeted using FISH. For example without limiting the scope of the present invention, messenger RNA (mRNA), DNA telomeres, other highly repeated DNA sequences, and other non-coding DNA sequencing can be targeted by FISH.

In another preferred embodiment, the present invention provides a composition comprising fluorescent semiconductor nanocrystals associated with a molecule or reagent for detection of biological compounds such as enzymes, enzyme substrates, enzyme inhibitors, cellular organelles, lipids, phospholipids, fatty acids, sterols, cell membranes, molecules involved in signal transduction, receptors and ion channels. The composition also can be used to detect cell morphology and fluid flow; cell viability, proliferation and function; endocytosis and exocytosis (Betz et al. *Curr Opin Neurobiol* 1996 June;6(3):365–71 incorporated herein by reference); and reactive oxygen species (e.g. superoxide, nitric oxide, hydroxyl radicals, oxygen radicals.) In addition, the composition can be used to detect hydrophobic or hydrophilic regions of biological systems.

Other applications of fluorescent markers in biological systems can be found in Haugland, R. P. Handbook of Fluorescent Probes and Research Chemicals (Molecular Probes. Eugene, Oreg. Sixth Ed. 1996; Website, www.probes.com) which is incorporated by reference in its entirety.

In another aspect of the invention, the present invention provides methods of detecting biological compounds using nanocrystals. Without limiting the scope of the present invention, the conjugation of nanocrystals to such molecules as small molecules, proteins, and nucleic acids allows the use of nanocrystals in any method of detecting the presence or amount of biological compounds. In addition, the present invention provides multiplexed assays and analytical methods of detecting biological states and/or compounds using molecules conjugated to different sizes, size distributions and/or compositions of semiconductor nanocrystals having a distinct emission spectral. The molecule conjugated to the nanocrystal is a first member of a binding pair that has specific affinity for a corresponding second member of the binding pair. In a multiplexed method, the presence of a plurality of target analytes are simultaneously detected in a one or more assay mixtures using up to 10–20 distinct semiconductor nanocrystal-binding pair conjugates. The conjugates are distinct from one another in at least two properties: (1) the emission spectrum of each member of the plurality of nanocrystals is distinguishable from the other members of thereof; and (2) the target analyte specificity of each member of the plurality of first member of the binding pairs is distinguishable from the other members thereof. Accordingly, up to 10–20 (e.g., 2, 3, 4, 5, 6, 7, 8, 9, 10, 11, 12, 13, 14, 15, 16, 17, 18, 19, or 20) different analytes, i.e., second members of the binding pairs, can be assayed simultaneously in the same or different assay mixture.

Certain particular methods are discussed below in order to highlight the advantages and utilities of the inventive compositions. These methods, include but are not limited to, fluorescence immunocytochemistry, fluorescence microscopy, DNA sequence analysis, fluorescence in situ hybridization (FISH), fluorescence resonance energy transfer (FRET), flow cytometry (Fluorescence Activated Cell Sorter; FACS) and diagnostic assays for biological systems.

Immunocytochemistry

Currently, fluorescence immunocytochemistry combined with fluorescence microscopy (e.g. confocol microscopy; for a review see, Mongan et al. *Methods Mol Biol* 1999;114:51–74; fluorescence correlated spectroscopy; for a review see Rigler. *J Biotechnol.* Jul. 31, 1995; 41(2–3):177–86, both of which are incorporated by reference) allows researchers to visualize biological moieties such as proteins and nucleic acids within a cell (see Current Protocols in Cell Biology, John Wiley & Sons, Inc., New York; for a review on fluorescence microscopy see Hasek and Streiblova. *Methods Mol Biol* 1996;53:391–405; both of which are incorporated herein by reference). One method uses primary antibodies hybridized to the desired in vivo target. Then, secondary antibodies conjugated with fluorescent dyes and targeted to the primary antibodies are used to tag the complex. The complex is visualized by exciting the dyes with a wavelength of light matched to the dye's excitation spectrum. Fluorescent dyes that interact with nucleic acids such as DAPI (4,6-diamidino-2-phenylindole), propidium iodide, ethidium bromide and Hoechst dyes (e.g., benzoxanthene yellow and bixbenzimide ((2'-[4-hydroxyphenyl]-5-[4-methyl-1-piperazinyl]-2,5'-bi-1H-benzimidazol) and (2'-[4-ethoxyphenyl]-5-[4-methyl-1-piperazinyl]-2,5'-bi-1H-benzimidazol)) are used to visualize DNA and RNA.

Fluorescent tags are also used to detect the presence and location of specific nucleic acid sequences. DNA sequences that are complementary to the target sequences are directly labeled with fluorescent nucleotides (e.g. fluorescein-12-dUTP) and used as probes to visualize the presence and location of the target nucleotide sequence. Examples of targets include messenger RNA and genomic DNA. Alternatively, the DNA probe can be labeled with a marker such as biotin or digoxygenin. Upon hybridization of the probe to its target sequence, a fluorescent-conjugated antibody raised against the marker (e.g. biotin or digoxygenin) is used to locate and visualize the probe.

Colocalization of biological moieties in a cell is performed using different sets of antibodies for each cellular target. For example, one cellular component can be targeted with a mouse monoclonal antibody and another component with a rabbit polyclonal antibody. These are designated as the primary antibody. Subsequently, secondary antibodies to the mouse antibody or the rabbit antibody, conjugated to different fluorescent dyes having different emission wavelengths, are used to visualize the cellular target. In addition, fluorescent molecules such as DAPI (4,6-diamidino-2-phenylindole) can target and stain biological moieties directly. An ideal combination of dyes for labeling multiple components within a cell would have well-resolved emission spectra. In addition, it would be desirable for this combination of dyes to have strong absorption at a coincident excitation wavelength.

Tunable nanocrystals are ideal for use in fluorescence immunocytochemistry. The absorption spectra of nanocrystals are broad. As a result, a single light source (in the UV-blue region, preferably in the blue region) can be used to excite all nanocrystals in a system simultaneously. This allows a researcher to visualize the location of all nanocrystals (and thus the biological components targeted) in a cell simultaneously. In addition, a single excitation light source simplifies the machinery involved in fluorescence excitation. Furthermore, the combination of narrow linewidths, and symmetrical, nearly gaussian lineshapes lacking a tailing region in the emission spectra of nanocrystals and the tunability of the emission wavelengths allows the use of multiple nanocrystal tags in one system. As a result, as many as 10–20 differently sized nanocrystals, each with different a emission spectrum, can be used simultaneously in one system, i.e., multiplexing, and more easily resolved with the use of techniques well known in the art, e.g., optically with or without the use of deconvolution software.

Immunoassay

One protocol for using semiconductor nanocrystals in heterogeneous immunoassays (assays in which the excess antibodies have to be removed in a separate step) is described in FIG. 1. An antibody to an antigen is adsorbed or covalently linked to a solid phase (see Current Protocols in Immunology, John Wiley & Sons, Inc., New York; incorporated herein by reference). Then the antigen is added and allowed to bind to the solid-phase antibody. After the excess antigen is removed, the matrix is reacted with nanocrystal-labeled antibody. After a second wash, the fluorescence can be quantified.

Figure 2:
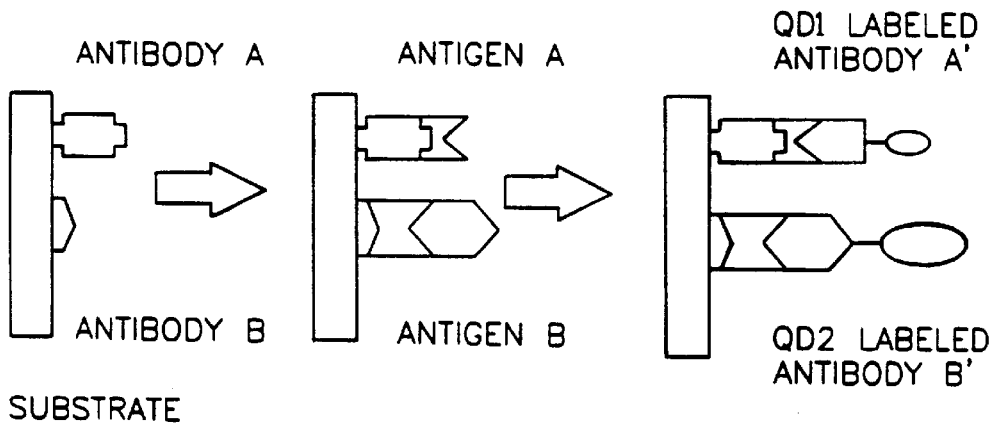
FIG. 2 is a pictorial depiction of the multicolored semiconductor nanocrystal labeled, parallel immunoassay.

This protocol is amenable to multiple, parallel immunoassaying schemes, i.e., multiplexing, as well (FIG. 2). A series of different antibodies is covalently linked to a substrate. Then disparate antibody specific antigens can be bound to this array. Finally, different antibodies labeled with specific-size, size distribution or composition nanocrystals are bound to the antigens. Again, the fluorescence from each different size, size distribution or composition nanocrystal can be quantified and the relative amount of each antigen determined. Such an extension should be possible as different sized, size distribution or composition nanocrystals not only have similar solubility properties, narrow linewidths and unique, size-dependent, size distribution-dependent and composition-dependent fluorescence frequencies, but also can be excited by the same source of radiation (in the UV-blue, preferably in the blue region of the spectrum).

High-throughput DNA Sequence Analyses

Semiconductor nanocrystals conjugated to nucleic acids have applications in non-cellular biological systems. As an example without limiting the scope of the invention, with the advent of fluorescently-labeled nucleotides, high-throughput DNA sequencing and DNA fragment analysis have become powerful tools in the analyses of DNA sequences (ABI system; Perkin-Elmer).

To describe these sequencing reactions briefly, four reactions are performed to determine the positions of the four nucleotide bases within a DNA sequence. Using a DNA sample as a template, a chain of DNA is synthesized from a pool of nucleotides containing the four deoxynucleotides and one additional dideoxynucleotide. For example, in the adenine sequencing reaction, DNA is synthesized from a mixture that includes all four deoxynucleotides (dATP, dGTP, dCTP, dTTP) plus dideoxyadenosine triphosphate (ddATP). The enzyme DNA polymerase will synthesize the new chain of DNA by linking dNTPs. Occasionally DNA polymerase will incorporate a ddATP instead of a dATP. The ddATP in the nascent chain will then terminate the synthesis of that chain of DNA due to the lack of the 3' hydroxyl group as a connection to the next dNTP. Thus the DNA products from the adenine sequencing reaction will be a heterogeneous mixture of DNA that vary in length with each chain terminated at a position corresponding to adenine.

The four DNA sequencing reactions are resolved by size by polyacrylamide gel electrophoresis. With singly radiolabeled ($^{32}P$ or $^{35}S$) DNA, the four reactions are loaded into four individual lanes. The resolved products of differing sizes result in a pattern of bands that indicate the identity of a base at each nucleotide position. This pattern across the four lanes can be read like a simple code corresponding to the nucleotide base sequence of the DNA template. With fluorescent dideoxynucleotides, samples containing all four dideoxynucleotide chain-terminating reactions can be loaded into a single lane. Resolution of the four dideoxynucleotide reactions is possible because of the different fluorescent labels for each sample. For example, ddATP can be conjugated with a green fluorescent tag. The other three ddNTP (dideoxynucleotide triphosphate) are tagged with three different fluorescent colors. Thus, each chain-terminating ddNTP is coded with a different color. When all four reactions are resolved in one lane on a DNA sequencing gel, the result is one ladder of bands having four different colors. Each fluorescent color corresponds to the identity of the nucleotide base and can be easily analyzed by automated systems.

However as previously discussed, multiple light sources are needed for excitation of the four different fluorescent organic dye markers. The use of semiconductor nanocrystals as the fluorescent tags for each dideoxynucleotide chain-terminating reaction simplifies the automation of high-throughput DNA sequencing since only a single light source is needed to excite all four fluorescent tags. In addition, multiplexing with semiconductor nanocrystals permits multiple sequencing reactions to be conducted and analyzed simultaneously, thereby further increasing the throughput of the assay.

In PCR (polymerase chain reaction)-based DNA typing and identification, short tandem repeat (STR) loci in the human genome are amplified by PCR using primers that are labeled with fluorescent tags. The size of these loci can differ or can coincide from person to person, or from individual subject to individual subject, and depends on genetic differences in the population. Usually multiple loci are examined. Any locus that shows a size difference with another sample conclusively indicates that the two samples are derived from two different individuals. However, demonstrating that two samples originate from the same individual is less conclusive. Unlike fingerprint patterns, the size of STR loci can coincide between two individuals. However, the statistical probability of multiple loci coinciding in size between two individuals decreases as the number of loci examined is increased. Using conventional organic fluorescent dyes, a limitation to the number of samples resolved in a single lane (and thus high-throughput) is the number of the fluorescent tags available and the resolution of the emission spectra. Increasing the resolution of the fluorescent tags thus would increase the capacity of the number of loci tested per lane on a gel.

Fluorescence Resonance Energy Transfer (FRET)

The present invention provides a method for detecting the proximity of two or more biological compounds. Long-range resonance energy transfer between nanocrystals and between a nanocrystal and an organic fluorescent dye can occur efficiently if the spacing between them is less than approximately 100 Å. This long-range effect can be exploited to study biological systems. (For reviews on FRET, see Clegg. *Curr Opin Biotechnol.* 1995 Feb;6(1):103–10; Clegg. *Methods Enzymol.* 1992;211:353–88; Wu and Brand. *Anal Biochem.* 1994 April;218(1):1–13; all are incorporated herein by reference). In particular, this effect can be used to determine the proximity of two or more biological compounds to each other. Conversely, this effect can be used to determine that two or more biological compounds are not in proximity to each other. Advantages to using nanocrystals combined with organic dyes for FRET include the ability to tune the narrow emission of the nanocrystals to match precisely the excitation wavelength of organic dyes, thus reducing background signals.

In a preferred embodiment, nanocrystals can be conjugated to a biological compound or a molecule that associates with a biological compound. A fluorescent organic dye is used to label a second biological compound or a second molecule that associates with a second biological compound. The nanocrystals are constructed to emit light at a wavelength that corresponds to the excitation wavelength of the organic dye. Therefore in the presence of excitation light tuned to the excitation wavelength of the nanocrystals and not the dye, when a first compound labeled with nanocrystals is in close proximity (<100 Å) to a second compound labeled with an organic dye, the emission of the nanocrystals will be absorbed by the dye resulting in excitation and fluorescence of the dye. Consequently, the color observed for this system will be the color of the fluorescent dye. If the first compound labeled with nanocrystals is not in close proximity to a second compound labeled with an organic dye that absorbs light at the wavelength emitted by the nanocrystals, the dye will not quench the emissions of the nanocrystals. Thus, the color of the system will coincide with the color of the fluorescent nanocrystals.

Figure 3:
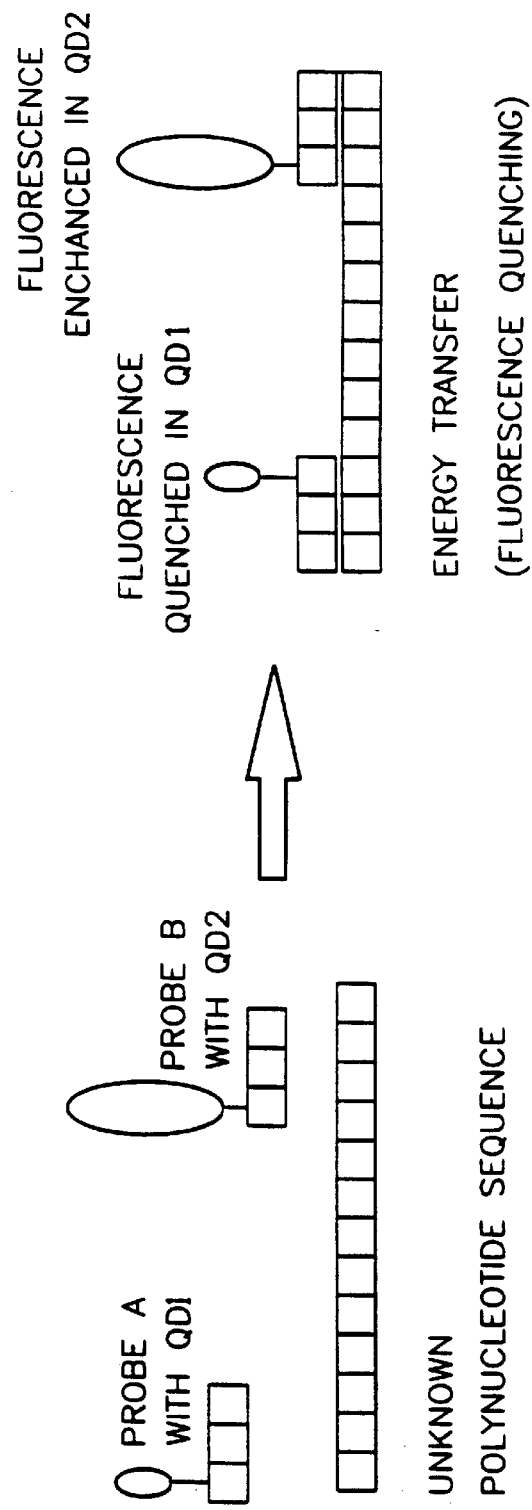
FIG. 3 a pictorial depiction of the use of two differently colored nanocrystals or one color nanocrystal and one organic dye to detect proximity of compounds. In this example, two oligonucleotide probes are hybridized to DNA sequences in close proximity and detected by fluorescence resonance energy transfer

As an example without limiting the scope of the invention, a first DNA probe is labeled with an organic fluorescent tag and hybridized to its target DNA sequence. A second DNA probe is labeled with nanocrystals that are tuned to emit light corresponding to the excitation wavelength of the organic fluorescent tag. If the second probe hybridizes to a target sequence that is within at certain distance (<100 Å) to the first probe, in the presence of excitation light tuned to the nanocrystals and not the dye, the fluorescent emission of the nanocrystals will excite the organic dye and thus provide a signal (color of the dye) indicating proximity of the two sequences (FIG. 3). A signal indicating a lack of close proximity between the two probes would be the color of the nanocrystals since the dye would not absorb the light emitted by the nanocrystals and therefore would not fluoresce.

Alternatively, two different sized nanocrystal labels are attached to probe nucleotide sequences. If these strands bind to the target DNA, then the emissions from the smaller size nanocrystals should be quenched while those from the larger sized ones should be enhanced. Spectroscopic quantification of this energy transfer effect could be done in situ. Hence automated detection of sets of DNA sequences could also be realized.

In another preferred embodiment, a method of detecting proteases using FRET can be exploited. A peptide with a protease cleavage site is synthesized to contain a nanocrystal on one side of the cleavage site and an organic fluorescent dye on the other side in close proximity such that the emission of the nanocrystal is absorbed by the dye and thus quenched. In the presence of the protease, the peptide will be cleaved, releasing the two halves of the peptide and removing the quenching effect of the fluorescent dye. Therefore, detection of emitted light from the nanocrystal indicates that cleavage of the peptide by the protease.

Use of Nanocrystals in Flow Cytometry/Fluorescence Activated Cell Sorter (FACS)

In this method (see Current Protocols in Cytometry and Current Protocols in Immunology, John Wiley & Sons, Inc., New York; both of which are incorporated herein by reference), cells are labeled with a fluorescent dye and then passed, in a suspending medium, through a narrow dropping nozzle so that each cell is in a small droplet. A laser based detector system is used to excite fluorescence and droplets with positively fluorescent cells are given an electric charge. Charged and uncharged droplets are separated as they fall between charged plates and so collect in different tubes. The machine can be used either as an analytical tool, counting the number of labeled cells in a population or to separate the cells for subsequent growth of the selected population. Further sophistication can be built into the system by using a second laser system at right angles to the first to look at a second fluorescent label or to gauge cell size on the basis of light scatter. The utility of the method is that it looks at large numbers of individual cells and makes possible the separation of populations with, for example a particular surface properties.

Nanocrystal technology can be applied to FACS. An advantage of using nanocrystals in FACS is that using a single excitation light source, multiple components can be tagged. Therefore, cells may be sorted using a variety of parameters.

Diagnostics in Biological Applications

Semiconductor nanocrystal technology can be used in diagnostic systems for biological applications. Currently, the use of antibodies conjugated to fluorescent organic dyes for detection of biological moieties such as white blood cells and viruses (e.g. HIV) has limitations associated with the physical and spectral properties of these dyes. These limitations, as previously discussed, include the spectral overlap observed when using multiple dyes with different emission spectra which contributes to the background when using fluorescent-conjugated antibodies as a diagnostic assay. Thus, the present invention provides a method of detecting biological moieties as a diagnostic assay for medical purposes. In a preferred embodiment, nanocrystals can be conjugated to molecules that are used to detect the presence and/or concentration of a biological compound for a diagnostic assay for medical purposes.

In a preferred embodiment, nanocrystals can be conjugated to antibodies to detect components in blood or plasma such white blood cells, viruses (e.g. HIV), bacteria, cell-surface antigens of cancer cells, and any biological component associated with human diseases and disorders. As with previously described biological applications of the nanocrystal technology, the use of multiple nanocrystal allows the high-throughput screening of samples.

There are many assays designed to detect the sequence of a DNA sample. Each of these methods share some or all of a set of common features. These features include: sequence specificity derived from complementary oligonucleotide hybridization or annealing; a solid support or solid phase which allows separation of specifically bound assay reagents; and a label which is used for detecting the presence or absence of the specific, intended assay interaction. Examples of assays designed to detect the sequence of a DNA sample can be found in U.S. Pat. No. 5,888,731 to Yager et al., U.S. Pat. No. 5,830,711 to Barany et al., U.S. Pat. No. 5,800,994 to Martinelli et al., U.S. Pat. No. 5,792,607 to Backman et al., U.S. Pat. No. 5,716,784 to Di Cesare, U.S. Pat. No. 5,578,458 to Caskey et al., U.S. Pat. No. 5,494,810 to Barany et al., U.S. Pat. No. 4,925,785 to Wang et al., U.S. Pat. No. 4,9898,617 to Landegren et al. Nucleic acid hybridization assays are described in, for example U.S. Pat. No. 5,681,697 to Urdea et al., U.S Pat. No. 5,124,246 to Urdea et al., U.S. Pat. No. 4,868,105 to Urdea et al., and European Patent Publication No. 70.685, inventors Heller et al.

A semiconductor nanocrystal conjugated to a oligonucleotide probe can be used to detect a nucleic acid analyte or the presence therein of a target nucleotide sequence using any method described in the aforementioned patents and patent publications, or any method know to a person of ordinary skill in the art. In addition, a plurality of distinct oligonucleotide probes, each of which is conjugated to a semiconductor nanocrystal having a distinct emission spectrum, can be used in a multiplexed assay to detect a plurality of nucleic acid analytes or a plurality of target nucleic acid sequences in a single oligonucleotide analyte.

Imaging Apparatus

The present invention also provides an apparatus for reading the output of biological substrates encoded with multicolor fluorescent markers. An automated apparatus that detects multicolored luminescent biological systems can be used to acquire an image of the multicolored fluorescent system and resolve it spectrally. Without limiting the scope of the invention, the apparatus can detect samples by imaging or scanning. Imaging is preferred since it is faster than scanning. Imaging involves capturing the complete fluorescent data in its entirety. Collecting fluorescent data by scanning involves moving the sample relative to a microscope objective.

There are three parts to the apparatus: 1) an excitation source, 2) a monochromator to spectrally resolve the image, or a set of narrow band filters, and 3) a detector array. This apparatus can be applied to biological systems such as individual cells, a population of cells, or with an array of DNA.

In a preferred embodiment, for excitation of fluorescent markers, the apparatus would consist of a blue or ultraviolet light source for excitation of the nanocrystals. Preferably, the wavelength of the light source is shorter than the wavelength of emissions of all nanocrystals. As an example without limiting the scope of the invention since alternative methods may be used to obtain similar results, preferably, the light source is a broadband UV-blue light source such as a deuterium lamp with a filter attached to it. Another approach is to derive the light source from the output of a white light source such as a xenon lamp or a deuterium lamp and pass the light through a monochromator to extract out the desired wavelengths. Alternatively, filters could be used to extract the desired wavelengths.

In another preferred embodiment for the excitation of fluorescent markers, any number of continuous wave gas lasers can be used. These include, but are not limited to, any of the argon ion laser lines (e.g. 457, 488, 514 um, etc.) or a HeCd laser. Furthermore, solid state diode lasers that have an output in the blue region of the spectrum such as GaN-based lasers or GaAs-based lasers with doubled output could be used. In addition, YAG or YLF-based lasers with doubled or tripled output, or any pulsed laser with an output also in the blue region can be used.

In a preferred embodiment, for the spectral resolution of the fluorescent nanocrystals in a system, preferably the luminescence from the nanocrystals is passed through an image-subtracting double monochromator. An alternative method of resolving the spectra of each nanocrystal in a system with multiple nanocrystals is to pass the luminescent light through two single monochromators with the second one reversed from the first. The double monochromator consists of two gratings or two prisms and a slit between the two gratings. The first grating spreads the colors spatially. The slit selects a small band of colors and the second grating recreates the image. This image contains only the colors specific to the output of a nanocrystal of a particular size (emission).

In another preferred embodiment for resolving the emission spectra of a system containing multiple nanocrystals is to use a computer-controlled color filter wheel where each filter is a narrow band filter centered at the wavelength of emission of one of the nanocrystals in a system.

In a preferred embodiment, the fluorescent images are recorded using a camera preferably fitted with a charge-coupled device. Any two-dimensional detector can be used. Software is then used to color the images artificially to the actual wavelengths observed. The system then moves the gratings to a new color and repeats the process. The final output consists of a set of images of the same spatial region, each colored to a particular wavelength. This provides the necessary information for rapid analysis of the data.

In another preferred embodiment, an alternative method of detecting the fluorescent nanocrystals in biological systems is to scan the samples. An apparatus using the scanning method of detection collects luminescent data from the sample relative to a microscope objective by moving either the sample or the objective. The resulting luminescence is passed thought a single monochromator, a grating or a prism to resolve the colors spectrally. Alternatively, filters could be used to resolve the colors spectrally.

For the scanning method of detection, the detector is a diode array which records the colors that are emitted at a particular spatial position. Software then recreates the scanned image, resulting in a single picture (file) containing all the colors of the nanocrystals in the sample.

Since an entire spectrum is captured in a single file, in systems with multiple nanocrystal, spectral deconvolution is necessary and easily performed to resolve overlapping spectra. As previously discussed, the narrow spectral linewidths and nearly gaussian symmetrical lineshapes lacking a tailing region observed for the emission spectra of nanocrystals combined with the tunability of the emission wavelengths of nanocrystals allows high spectral resolution in a system with multiple nanocrystals. In theory, up to 10–20 different-sized nanocrystals from different preparations of nanocrystals, with each sample having a different emission spectrum, can be used simultaneously in one system with the overlapping spectra easily resolved using deconvolution software.

Photoluminescence of Single Semiconductor Nanocrystals

Single semiconductor nanocrystals have detectable luminescence (Nirmal et al. Nature 383: 802, 1996; and Empedocles et al. Phys. Rev. Lett. 77:3873, 1996; both incorporated herein by reference) which can be applied to biological systems. An advantage of having highly fluorescent single nanocrystals that are detectable and associated with biological compounds is that this allows the detection of very small quantities of biological molecules. Thus, the throughput of assays that screen large numbers of samples can be improved by utilizing single nanocrystals associated with biological compounds to decrease the sample size, and consequently allowing a greater number of samples to be screen at any one time.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

The following examples are intended to provide those of ordinary skill in the art with a complete disclosure and description of how to make and use the novel compositions of the invention, and are not intended to limit the scope of what the inventors regard as their invention in any way. Efforts have been made to ensure accuracy with respect to numbers used (e.g., amounts, temperatures, etc), but some experimental error and deviation should, of course, be allowed for. Unless indicated otherwise, parts are parts by weight, temperatures are in degrees centigrade, and pressure is at or near atmospheric.

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); and a series, *Methods in Enzymology* (Academic Press, Inc.); Kirk-Othmer's *Encyclopedia of Chemical Technology;* House's *Modern Synthetic Reactions;* the Marvel et al. text ORGANIC SYNTHESIS; Collective Volume 1, and the like.

EXAMPLES

Example 1

Preparation of TOPO Capped-(CdSe)ZnS (a) Preparation of CdSe

Trioctylphosphine oxide (TOPO, 90% pure) and trioctylphosphine (TOP, 95% pure) were obtained from Strem and Fluka, respectively. Dimethyl cadmium ($CdMe_2$) and diethyl zinc ($ZnEt_2$) were purchased from Alfa and Fluka, respectively, and both materials were filtered separately through a 0.2 micron filter in an inert atmosphere box.

Trioctylphosphine selenide was prepare by dissolving 0.1 mols of Se shot in 100 ml of TOP thus producing a 1 M solution of TOPSe. Hexamethyl(disilathiane) (TMS$_2$S) was used as purchased from Aldrich. HPLC grade n-hexane, methanol, pyridine and n-butanol were purchased from EM Sciences.

The typical preparation of TOP/TOPO capped CdSe nanocrystals follows. TOPO (30 g) was placed in a flask and dried under vacuum (about 1 Torr) at 180 degrees C. for 1 hour. The flask was then filled with nitrogen and heated to 350 degrees C. In an inert atmosphere drybox the following injection solution was prepared: CdMe$_2$ (200 microliters, 2.78 mmol), 1 M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep yellow/orange solution with a sharp absorption feature at 470500 nm and a sudden temperature decrease to about 240 degrees C. Heating was restored to the reaction flask and the temperature was gradually raised to 260–280 degrees C.

Aliquots of the reaction solution were removed at regular intervals (510 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 510 degrees C. in response to an increase in the size distribution. Alternatively, the reaction can also be stopped at this point. When growth appears to stop, the temperature is raised 510 degrees C. When the desired absorption characteristics were observed, the reaction flask was allowed to cool to about 60 degrees C. and 20 mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

(b) Preparation of (CdSe)ZnS

A flask containing 5 g of TOPO was heated to 190 degrees C. under vacuum for several hours then cooled to 60 degrees C. after which 0.5 mL trioctylphosphine (TOP) was added. Roughly 0.1–0.4 micromols of CdSe nanocyrstals dispersed in hexane were transferred into the reaction vessel via syringe and the solvent was pumped off.

Diethyl zinc (ZnEt$_2$) and hexamethyldisilathiane ((TMS)$_2$S) were used as the Zn and S precursors, respectively. The amounts of Zn and S precursors needed to grow a ZnS shell of desired thickness for each CdSe sample were determined as follows: First, the average radius of the CdSe nanocrystals was estimated from TEM or SAXS measurements. Next, the ratio of ZnS to CdSe necessary to form a shell of desired thickness was calculated based on the ratio of the shell volume to that of the core assuming a spherical core and shell and taking into account the bulk lattice parameters of CdSe and ZnS. For larger particles the ratio of Zn to Cd necessary to achieve the same thickness shell is less than for the smaller nanocrystals. The actual amount of ZnS that grows onto the CdSe cores was generally less than the amount added due to incomplete reaction of the precursors and to loss of some material on the walls of the flask during the addition.

Equimolar amounts of the precursors were dissolved in 2–4 mL TOP inside an inert atmosphere glove box. The precursor solution was loaded into a syringe and transferred to an addition funnel attached to the reaction flask. The reaction flask containing CdSe nanocrystals dispersed in TOPO and TOP was heated under an atmosphere of N$_2$. The temperature at which the precursors were added ranged from 140 degrees C. for 23 Å diameter nanocrystals to 220 degrees C. for 55 Å diameter nanocrystals. When the desired temperature was reached the Zn and S precursors were added dropwise to the vigorously stirring reaction mixture over a period of 5–10 minutes.

After the addition was complete the mixture was cooled to 90 degrees C. and left stirring for several hours. Butanol (SmL) was added to the mixture to prevent the TOPO from solidifying upon cooling to room temperature. The overcoated particles were stored in their growth solution to ensure that the surface of the nanocrystals remained passivated with TOPO. They were later recovered in powder form by precipitating with methanol and redispersing into a variety of solvents including hexane, chloroform, toluene, THF and pyridine.

Example 2
Preparation of a Water-soluble Semiconductor Nanocrystals Using Long Chain Mercaptocarboxylic Acid TOPO capped-(CdSe)ZnS semiconductor nanocrystals were prepared as described in Example 1. The overcoated (CdSe)ZnS nanocrystals were precipitated from the growth solution using a mixture of butanol and methanol. To obtain the precipitated semiconductor nanocrystals, the solution was centrifuged for 5–10 min, the supernatant was decanted and the residue was washed with methanol (2×).

The residue was weighed. The weight of the TOPO cap was assumed to be 30% of the total weight; and a 30-fold molar excess of the new capping compound, 11-mercaptoundecanoic acid (MUA) was added. The residue and MUA (neat solution) were stirred at 60 degrees C. for 8–12 hours. A volume of tetrahydrofuran (THF) equal to the added MUA was added to the MUA/nanocrystal mixture, with the mixture was still hot. A clear solution resulted and the coated semiconductor nanocrystals were stored under THF.

Figure 4:
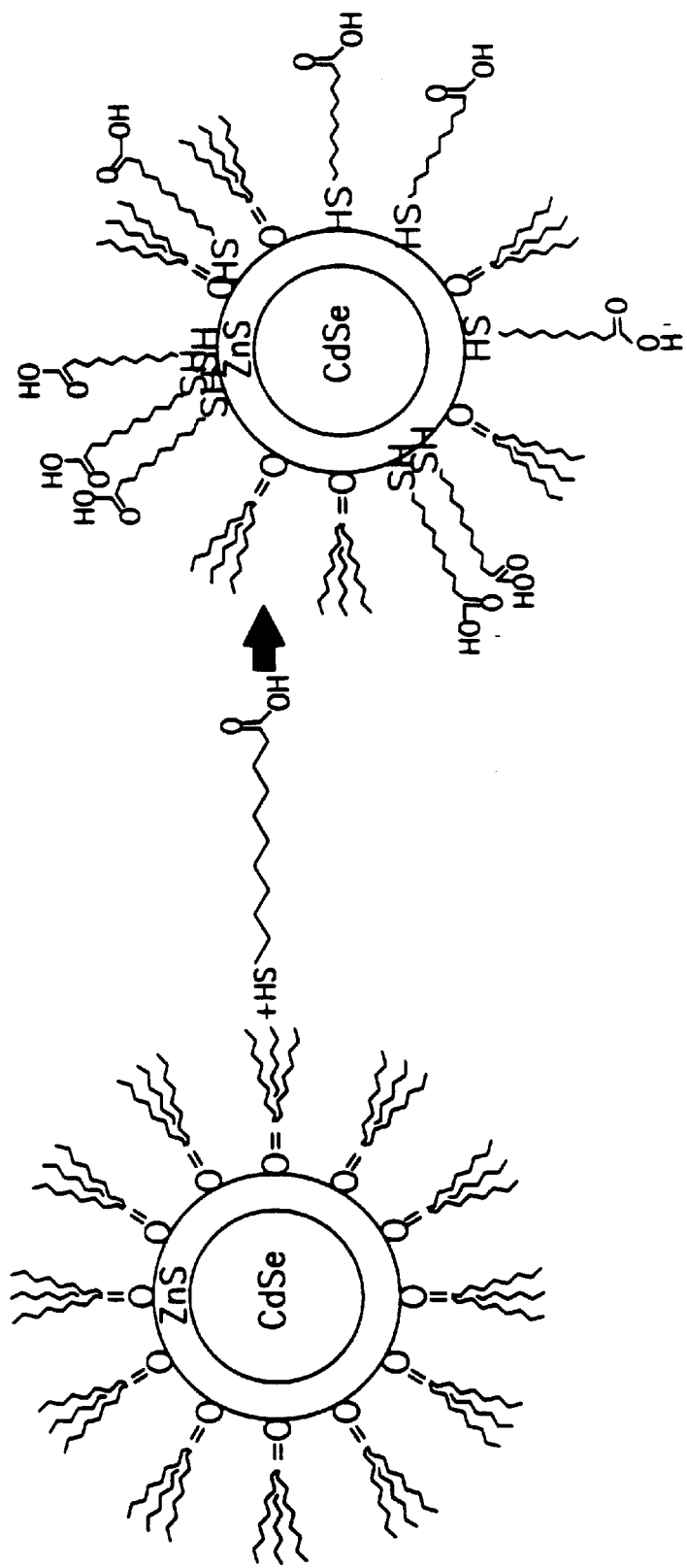
FIG. 4 is a pictorial depiction of the formation of water-soluble semiconductor nanocrystals by cap exchange

The coated semiconductor nanocrystals are rendered water-soluble by deprotonation of the carboxylic acid functional group of the MUA (FIG. 4). The deprotonation was accomplished by adding a suspension of potassium t-butoxide in THF to the MUA-semiconductor nanocrystal/THF solution. A gel resulted, which was then centrifuged and the supernatant liquid was poured off. The residue was washed twice with THF, centrifuged each time and the supernatant liquid poured off. The final residue was allowed to dry in air for 10 minutes. Deionized water (Millipore) was added to the residue until a clear solution formed.

The resultant coated semiconductor nanocrystals were tested for photoluminescent quantum yield. A CdSe semiconductor nanocrystal with a four monolayer coating of ZnS coated as described had an absorption band a 480 nm and a photoluminescent band at 500 nm, with a quantum yield of 12%. A second CdSe semiconductor nanocrystal with a four monolayer coating of ZnS coated as described had an absorption band a 526 nm and a photoluminescent band at 542 nm, with a quantum yield of 18%.

Example 3
Associating a Water-Solubilzed Semiconductor Nanocrystal With a Protein CdSe semiconductor nanocrystals overcoated with ZnS were synthesized, purified, and solubilized in water as previously described. Samples used in this experiment had 40 Å diameter CdSe cores, a ZnS shell which was nominally 4 monolayers (about 9 Å) thick, and capped with 11mercaptoundecanoic acid (MUA).

The following three reagents were mixed: 5.8 mg of 1-ethyl-3-(3-dimethylaminopropyl)carbodiimide hydrochloride (EDAC), 2.4 mg of Nhydroxysuccinimide (NHS), and 4 mL of a 0.82 micromolar solution of avidin in Millipore filtered water. The initially acidic mixture was treated with 0.1 M NaOH (aq) to adjust the pH to 7.6. Then 3 mL of a 2.1 micromolar aqueous solution of (CdSe)ZnS semiconductor nanocrystals was added. The mixture was stirred for 1 hour at room temperature. Excess reagents were quenched with 1 drop of 0.25 M ethanolamine in water.

To determine whether avidin coupling was successful, the colored reaction solution was passed through a short column containing biotin-coated acrylic beads. The filtrate which emerged was nearly colorless. The column was then washed with 10-fold volume of water. Under excitation with ultraviolet light, the beads displayed strong fluorescence due to the bound semiconductor nanocrystals, indicating successful coupling to avidin. A control experiment using only semiconductor nanocrystals and avidin with reagents to couple them (i.e., no EDAC or NHS) produced beads with little or no fluorescence, confirming that without avidin-coupling the semiconductor nanocrystals do not bind to the biotin coated beads.

Example 4
Biotin Hexane Dithiol (BHDT) Formation

Figure 5:
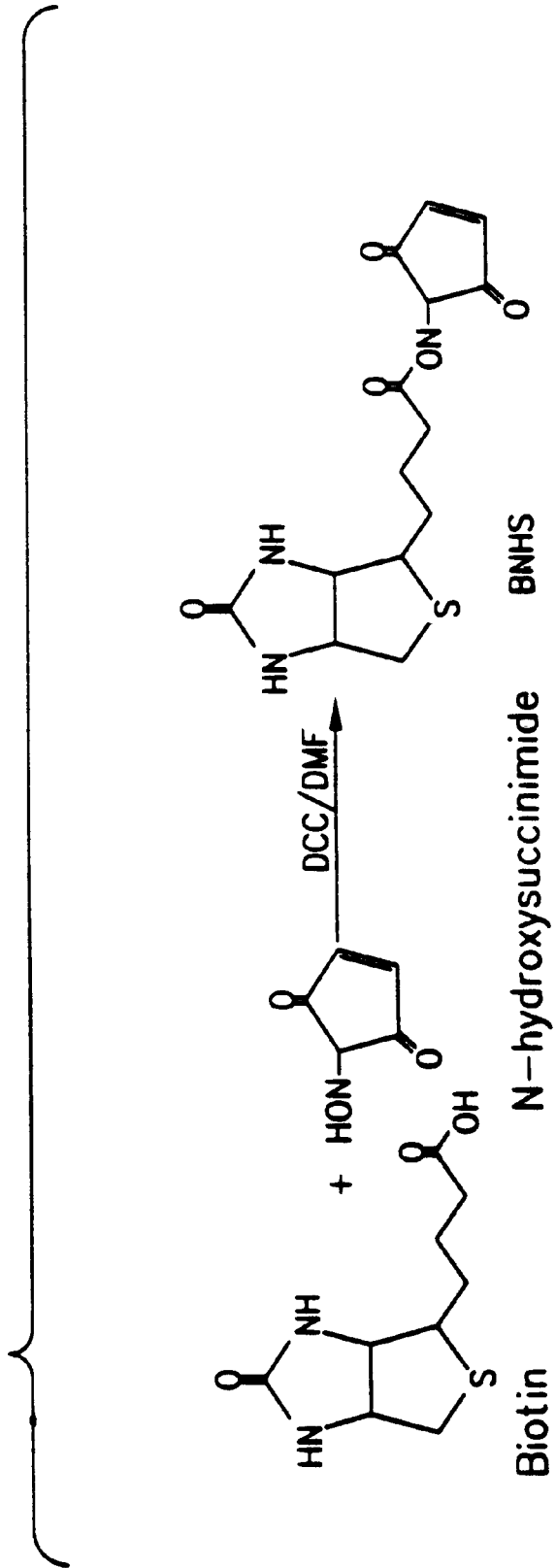
FIG. 5 and FIG. 6 illustrate an outline of the reaction between biotin and hexane dithiol to form the biotin-hexane dithiol (BHDT) derivative.
Figure 6:
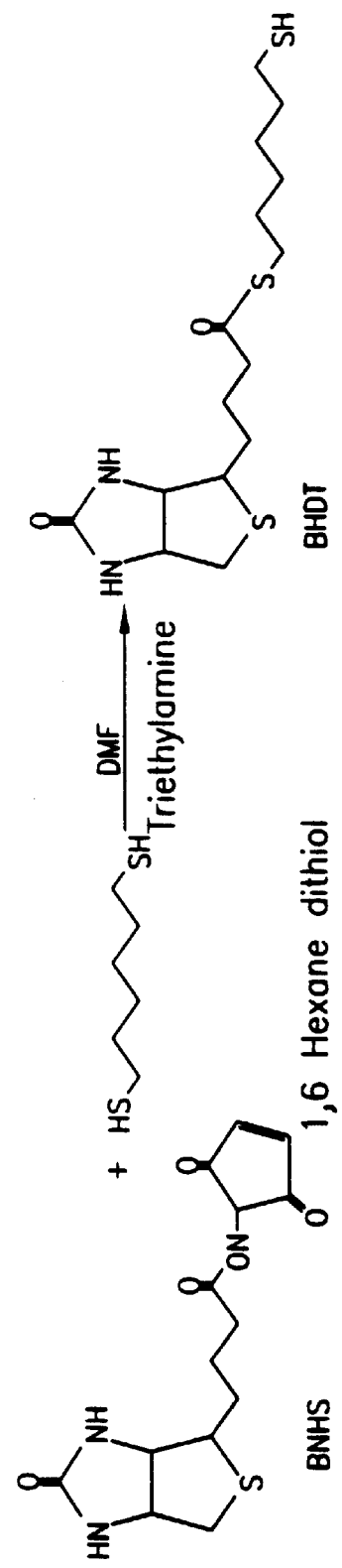

This procedure exploits the activated carboxylic acid group present in the biotin derivative, biotin-N-hydroxysuccinimide (BNHS; Pierce Chemicals, Rockford, Ill.) to made a biotin derivative which terminates in a thiol (SH) group (FIGS. 5 and 6). The presence of a thiol group is desired because thiols, in general, tend to adsorb to metal surfaces. Therefore, the thiol linkage can be exploited to attach biotin to the water-soluble semiconductor nanocrystals.

BNHS was dissolved in DMF and a 10-fold excess of 1,6-hexanedithiol was added in the presence of a weak base (triethylamine). The solution was stirred at room temperature for 16 hours. An NHS precipitate results and the solution was filtered to remove this NHS precipitate. The precipitate was washed with DMF. The precipitate was reduced to a minimum volume by removing solvent under a vacuum. Ether was then added to the concentrated solution to precipitate crude product. The product was isolated by filtration and the residue was pumped under a vacuum to remove the excess dithiol. A white powder (BHDT) was isolated and stored in the glove-box refrigerator to prevent thiol oxidation into disulfide. The resultant yield was approximately 68%.

Example 5
Biotin-amine Formation

Figure 7:
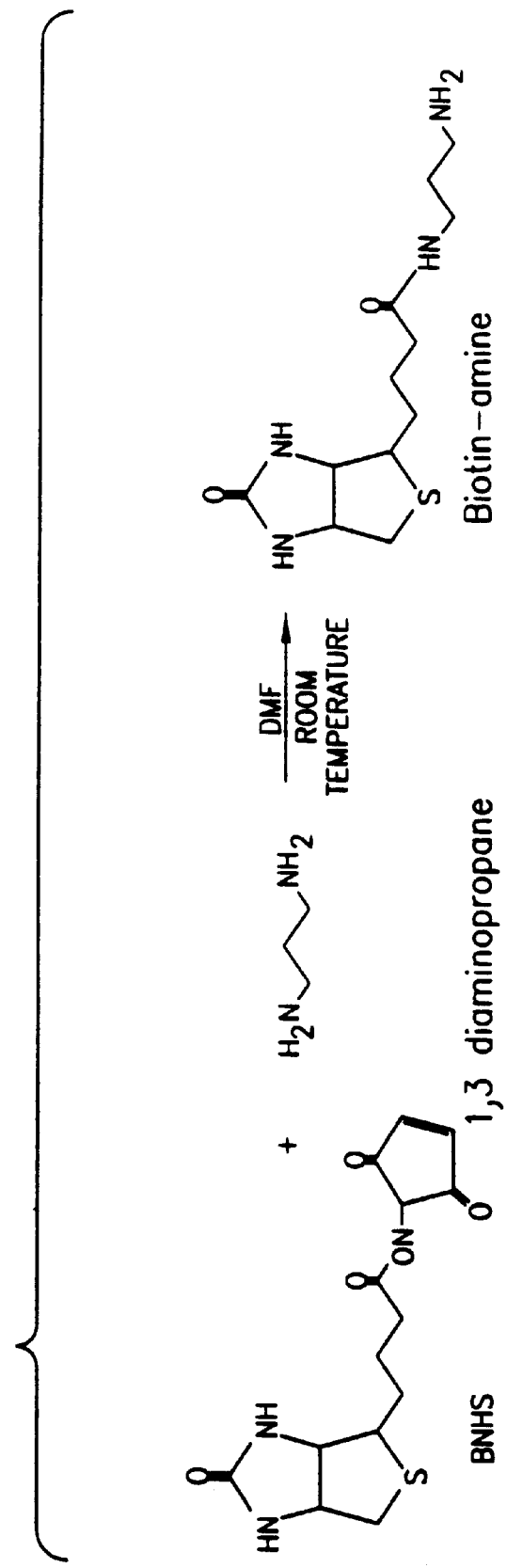
FIG. 7 is an outline of the reaction between biotin and a diamine to form biotin-amine derivative.

The philosophy of this procedure is similar to the one described in Example 6. In this example, the activated carboxylic group in biotin is utilized to make a biotin derivative with a terminal amine group (FIG. 7). As with thiols, amines conjugate to metal surfaces and can be used to attach biotin to the nanocrystals.

100 mg of BNHS was added to 2 ml DMF in a vial and mixed until all the BNHS had dissolved. Next, 0.9 ml of 1,3 diaminopropane (a 30 fold excess) was added to another vial. The BNHS/DMF solution was pipetted into the vial containing the neat 1,3-diaminopropane in 2 aliquots. The additions were performed in approximately 2 minutes and were spaced by 5 minutes. The resulting solution was stirred at room temperature for 24 hours, and a white precipitate (NHS) was formed. The NHS precipitate was removed by centrifuging, and the clear supernatant was transferred to another vial. Excess ether was added to the supernatant. Upon shaking, an immiscible layer was formed at the bottom which was transferred to a round-bottomed flask. DMF and excess diamine were then removed under vacuum to yield a white powder. The resultant yield was approximately 72%.

Example 6
Biotin-thiol-nanocrystal Complex Formation

Figure 8:
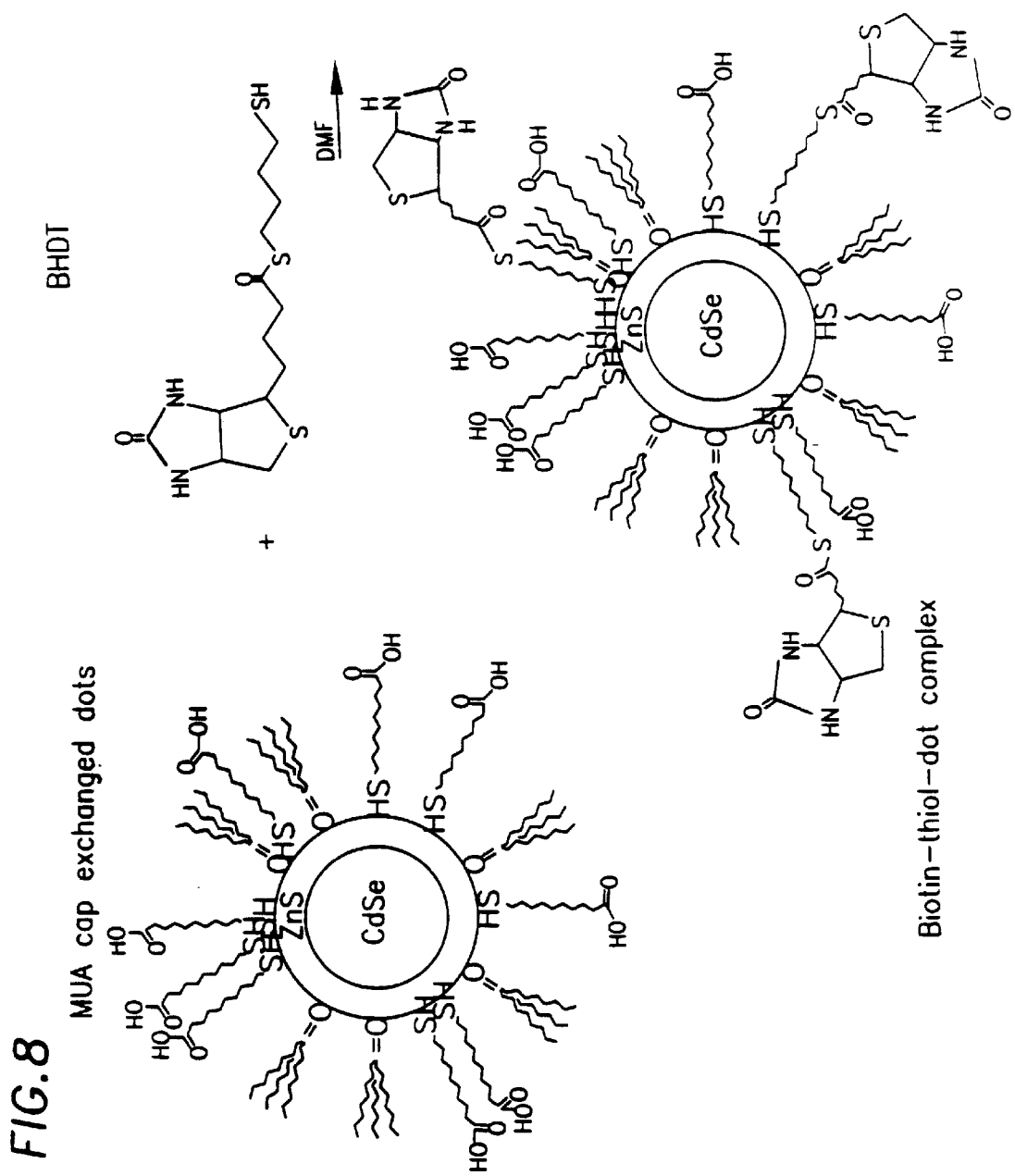
FIG. 8 depicts the formation of the biotin-thiol-nanocrystal complex for a water-soluble nanocrystal.

The aim of this protocol is to attach a biotin cap onto the surface of the semiconductor nanocrystals. The thiol end group of BHDT should adsorb to the nanocrystal surface (FIG. 8). Excess MUA from the cap was removed from the semiconductor nanocrystal/THF solution by precipitating the nanocrystals with a hexane/butanol mixture. The precipitate was redispersed in DMF and then precipitated again with a hexane/BuOH mixture. The precipitate was allowed to dry in air for 20–25 minutes, weighed, and redissolved in DMF. To calculate the amount of BHDT to dissolve in DMF, it was estimated that 30% of the total weight of the nanocrystal was derived from the cap. With that estimation, a 10-fold excess of BHDT (relative to the cap) was dissolved in DMF in a separate vial. The BHDT solution was then added to the nanocrystal/DMF solution over a 5 minute period. This mixture was stirred at room temperature for approximately 15 hours. The reaction was stopped by centrifugation, saving only the supernatant. A solution of potassium tert-butoxide in DMF was used to deprotonate the MUA acid cap. A colored precipitate was formed which is the water-soluble product. This mixture was subjected to centrifugation and the clear supernatant was discarded. No photoluminescence was observed from this layer indicating that all nanocrystals were successfully precipitated out of solution.

Figure 9:
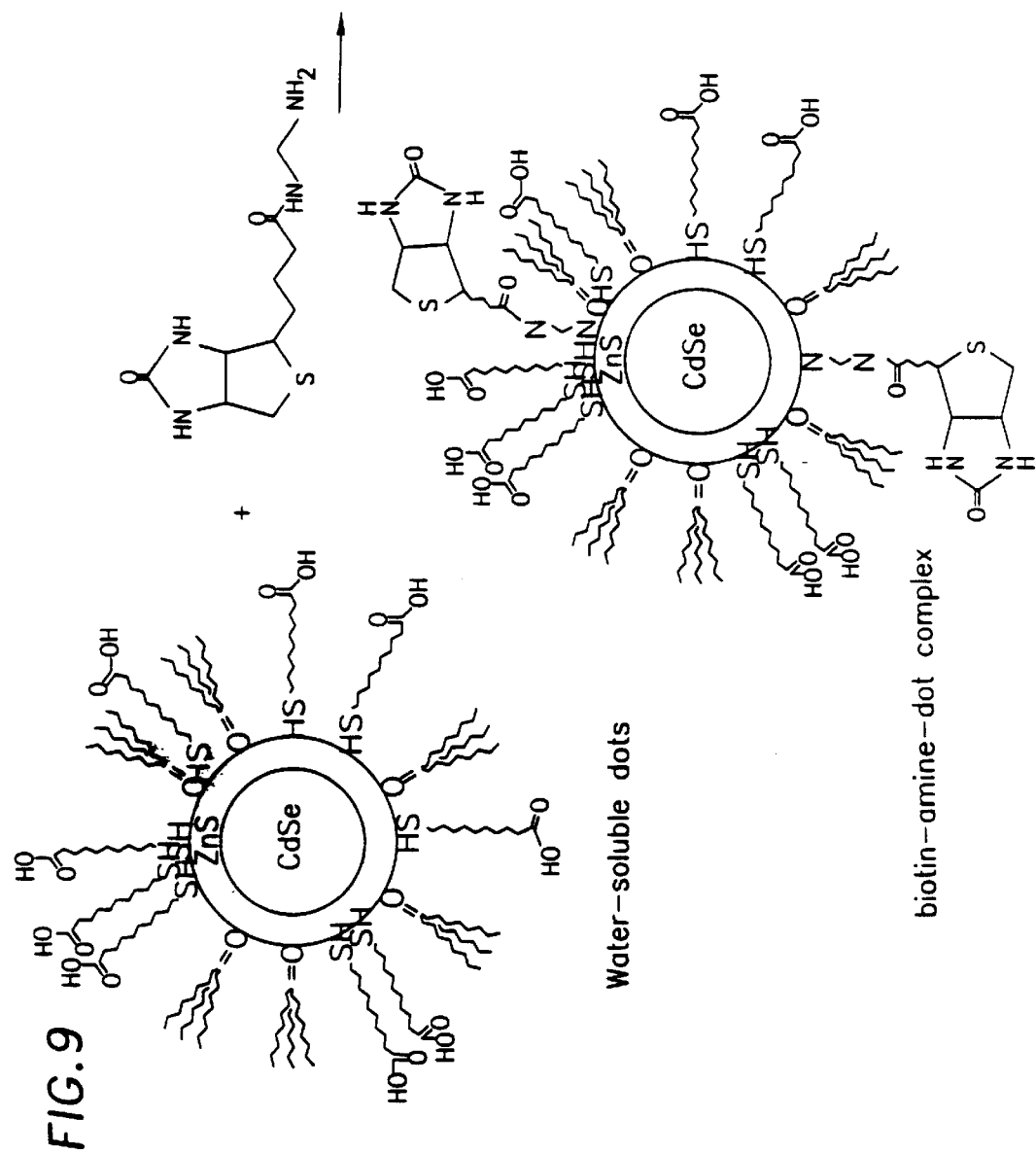
FIG. 9 depicts the formation of the biotin-amine-nanocrystal complex where the amine is adsorbed to the layer of the nanocrystal.

The precipitate was dissolved in deionized $H_2O$ (Millipore; Bedford, Mass.). The resulting solution was filtered through a 0.2 micron filter (Millipore), and transferred to a Ultrafree4 concentrator (Millipore). The solution was spun three times through the concentrator, and after each spin, the tubes were topped off with water. The concentrated solution was transferred to a vial and diluted with water. To confirm that biotin was successfully conjugated to the nanocrystals, the resulting solution was passed over an immobilized avidin column (Ultra-link, Pierce, Rockford, Ill.). Nanocrystals derivatized with biotin were retained by the column, resulting in the fluorescence of the column when illuminated with a UV-lamp. Control columns, which had non-biotinylated nanocrystals passed over them, showed no fluorescence when illuminated with a UV lamp Example 7
Biotin-amine-nanocrystal Complex Formation This protocol allows one to attach biotin to the surface of the semiconductor nanocrystals. Conjugation of biotin to the nanocrystals is achieved through the primary amine group at the end of biotin. Again, the affinity of the amine group for the surface of the nanocrystal is being exploited in this protocol (FIG. 9).

In this protocol, the MUA-capped nanocrystals were precipitated from the nanocrystal/THF solution using a hexane/BuOH mixture. The nanocrystals were air-dried for approximately 5 minutes and weighed. Deprotonation of the nanocrystals was accomplished by adjusting the pH of the solution to 10.5 with a 1M solution of $NH_4OH$. To calculate the amount of excess biotin-amine to use, it was estimated that 30% of the overall weight of the nanocrystals was derived from the cap. As such, a 10-fold excess (to the cap) of the biotin-amine reagent that was previously synthesized as in Example 5 was weighed out in a separate vial. This biotin derivative was then dissolved in a minimum volume of water. The solution containing the biotin-amine conjugate was pipetted into the solution of deprotonated nanocrystals over the course of about 3 minutes, and then stirred at room temperature for approximately 12 hours. The reaction was stopped by centrifugation, and the resulting supernatant was passed through a 0.2 micron filter (Millipore).

After filtration, the solution was transferred to a Ultrafree4 concentrator (Millipore; MW cutoff=30 kDa). The solution was spun three times through the concentrator, and after each spin, the tubes were topped off with deionized water. The final concentrated solution was diluted again with water and refiltered through a 0.2 micron filter. The resulting clear solution was passed over an immobilized avidin column (Ultra-link matrix; Pierce) to confirm biotinylation of the nanocrystals as described in Example 6.

Example 8
Biotin-amine-nanocrystal Complex Formation (Alternate Route)

Figure 10:
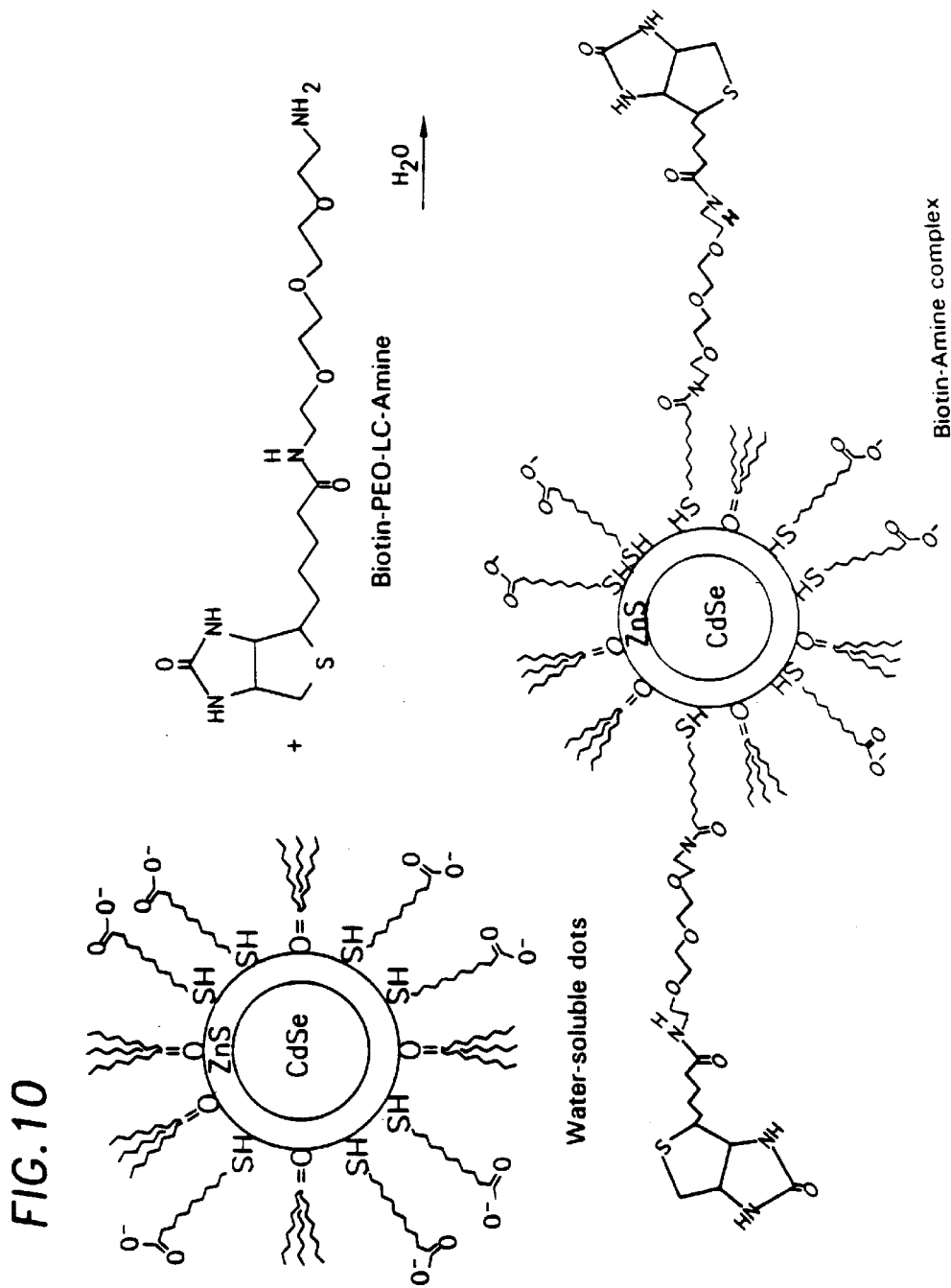
FIG. 10 depicts the formation of the biotin-amine-nanocrystal complex where the amine is conjugated to the carboxylic acid group of the water-solubilizing layer.

Unlike the procedures described in the previous Examples, this protocol utilizes the carboxylic acid groups that cap the surface of the water-soluble nanocrystals described in Example 2 (see FIG. 10). An amide bond is formed by conjugating a biotin-primary amine derivative to the carboxylic acid group at the surface of the nanocrystals. This coupling is done with the aid of 1-ethyl-3-(3-dimethylaminopropyl)carboimide hydrochloride (EDC; Pierce Chemicals, MW=191.7 g/mol), another group that activates the carboxylic acid group for use in subsequent reactions.

The MUA-capped nanocrystals dissolved in THF were precipitated by deprotonating the carboxylic acid group. This deprotonation was accomplished by adding a potassium tert-butoxide/THF suspension. The resulting residue was washed with THF twice, air-dried for 10–15 minutes, and weighed. Deionized water was then added to the residue and the suspension was shaken until the residue was completely dissolved. An aliquot from this solution was then concentrated by centrifugation three times using an Ultrafree4 concentrator (Millipore). Again, after each concentration, the tube was topped off with Millipore filtered water. The pH of the solution was adjusted to 9 using a 1M solution of $NH_4OH$.

For the following calculations, the weight of the acid cap was assumed to be 30% of the total weight of the nanocrystals. A solution of EZ-Link biotin-PEO-LC-Amine (Pierce Chemicals, MW=418 g/mol) and (1-ethyl-3-(3-dimethylaminopropyl)carboimide hydrochloride (EDC) in water at a molar equivalent of 1:1 (biotin derivative:acid cap) and 10:1 (EDC: acid cap) was then added to the nanocrystals (pH=8.5). This mixture was stirred at room temperature for 2–3 hours. The reaction was stopped by filtering the solution through a 0.2 micron Millipore filter twice.

As in Example 6, conjugation of biotin to the nanocrystals was confirmed by passing the sample over an avidin column. Successful conjugation resulted in a fluorescent column. A control column with non-biotinylated nanocrystals passed over it did not fluoresce.

Example 9
Semiconductor Nanocrystal-Oligonucleotide Complex Formation

This procedure is derived from the synthesis of the biotin-amine-nanocrystal complex. In particular, molar equivalents used in Example 5 is used to complex the semiconductor nanocrystals to 5' amine-labeled oligonucleotides.

A solution of MUA-capped nanocrystals dissolved in THF is deprotonated using potassium tert-butoxide. The resulting gel is washed with THF twice, centrifuged, and the subsequent supernatant discarded. The final residue is air-dried and weighed. Deionized water is added to the dried residue and shaken until a clear solution results. An aliquot of the solution is desalted and concentrated twice using an Ultrafree4 concentrator (Millipore). After each concentration, the concentrator tube is topped off with deionized water.

The amount of nanocrystals is estimated from the ratio of volumes of the aliquot and the total volume of water used. Relative to the amount of nanocrystals, one molar equivalent of 5' amine-labeled oligonucleotide and 10 molar equivalents of EDC (Pierce, mol wt=192) are dissolved in water. The pH of this solution is adjusted to 8.5. This solution is then added to the solution of nanocrystals described in the preceding section and stirred at room temperature for 2–3 hours. The reaction is stopped by passing the solution through 0.2 micron Millipore filter, and concentrating the filtrate using an Ultrafree4 concentrator.

Conjugation of the nanocrystals to the oligonucleotide is checked using a protocol described in the next Example.

Example 10
Semiconductor Nanocrystal-Oligonucleotide Complex Formation Check

The same column used to confirm biotin-nanocrystal formation can be modified to check for oligo-nanocrystal complex formation. A solution of 5' biotin-labeled oligonucleotide, complementary in sequence to the oligonucleotide complexed with the nanocrystals, is passed through an Ultra-link (Pierce Chemicals) immobilized avidin column. The biotin binds to the avidin to form an immobilized, oligonucleotide column. The oligonucleotide-nanocrystal conjugation is then be checked by passing the solution of the oligonucleotide-nanocrystal complex over this column. Complementary DNA sequences will be allowed to hybridize at the appropriate hybridization temperature for 12 hours as calculated by standard methods (Sambrook et al., Molecular Cloning: A Laboratory Manual, Cold Spring Harbor Laboratory Press, Cold Spring Harbor, N.Y., 1989; incorporated herein by reference). After hybridization, the column will be washed with water to remove any unbound oligonucleotide-nanocrystal complexes. Successful oligonucleotide-nanocrystal conjugation and subsequent hybridization to the complementary oligonucleotide column should result in a column that fluoresces with the appropriate excitation light. No fluorescence suggests all the color disappeared upon elution and that no complex was formed between the nanocrystals and the oligonucleotide.

What is claimed is:

1. A composition comprising:
   a first member of a binding pair;
   a semiconductor nanocrystal core linked to the first member, and
   an outer layer including a ligand comprising a multidentate molecule or a molecule having structural formula (I),

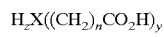    (I)

or a salt thereof, wherein:

X is the first portion of the ligand and is N, P or O=P;

n is greater than or equal to 6; and z and y are selected to satisfy the valence requirements of X.

2. The composition of claim 1, further comprises:

a shell layer overcoating the nanocrystal core, the shell comprising a semiconductor material having a band gap greater than that of the nanocrystal core.

3. The composition of claim 1 or 2, wherein the link between the first member of the binding pair and the nanocrystal is an interaction selected from the group consisting of covalent, noncovalent, hydrophobic, hydrophilic, electrostatic, magnetic or coordination through a metal complex.

4. The composition of claim 1 or 2, wherein the ligand includes a first portion comprising at least one linking group for attachment to the nanocrystal and a second portion comprising at least one hydrophilic group spaced apart from the linking group by a hydrophobic region sufficient to prevent electron charge transfer across the hydrophobic region.

5. The composition of claim 4, wherein the first member of the binding pair is linked to the second portion of the ligand.

6. The composition of claim 5, wherein the hydrophilic group is selected from the group consisting of a carboxylate, a sulfonate, a phosphate, polyethylene glycol or other polyol, hydroxide, an alkoxide, an ammonium salt, phosphate and phosphonate.

7. The composition of claim 5, wherein the first member is a protein, an oligonucleotide, an enzyme inhibitor, a polysaccharide or a small molecule having a molecular weight of less than about 1500 grams/mole.

8. The composition of claim 5, wherein the first member is an antibody, avidin, streptavidin, biotin or anti-digoxiginen.

9. The composition of claim 4, wherein the first portion of the ligand comprises a moiety selected form the group consisting of amines, thiols, phosphines, phosphine oxides, and amine oxides.

10. The composition of claim 4, wherein the nanocrystal core is a Group II–VI, Group III–V or Group IV semiconductor.

11. The composition of claim 10, wherein the core is a member of a monodisperse particle population.

12. The composition of claim 11, wherein the monodisperse particle population is characterized in that when irradiated the population emits light in a spectral range less than about 40 nm full width at half maximum (FWHM).

13. The composition of claim 12, wherein the monodisperse particle population is characterized in that when irradiated the population emits light in a spectral range less than about 25 nm full width at half maximum (FWHM).

14. The composition of claim 11, wherein the monodisperse particle population is characterized in that it exhibits no more than about a 10% rms deviation in the diameter of the core.

15. The composition of claim 14, wherein the monodisperse particle population is characterized in that it exhibits no more than about 5% rms deviation in the diameter of the core.

16. The composition of claim 4, wherein the core comprises CdS, CdSe, CdTe, ZnS, ZnSe, ZnTe, MgTe, GaAs, GaP, GaSb, GaN, HgS, HgSe, HgTe, InAs, InP, InSb, InN, AlAs, AlP, AlSb, AlS, PbS, PbSe, Ge, Si, an alloy thereof, or a mixture thereof.

17. The composition of claim 16, wherein the shell comprises ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, an alloy thereof, or a mixture thereof.

18. The composition of claim 4, wherein the core is CdSe and the shell is ZnS.

19. The composition of claim 18, wherein the core is a member of a monodisperse particle population.

20. The composition of claim 19, wherein the monodisperse particle population is characterized in that when irradiated the population emits light in a spectral range less than about 40 nm full width at half maximum (FWHM).

21. The composition of claim 20, wherein the monodisperse particle population is characterized in that when irradiated the population emits light in a spectral range less than about 25 nm full width at half maximum (FWHM).

22. The composition of claims 19, wherein the monodisperse particle population is characterized in that it exhibits no more than about a 10% rms deviation in the diameter of the core.

23. The composition of claim 22, wherein the monodisperse particle population is characterized in that it exhibits no more than about 5% rms deviation in the diameter of the core.

24. The composition of claim 18, wherein the core is a member of a monodisperse particle population.

25. The composition of claim 24, wherein the monodisperse particle population is characterized in that when irradiated the population emits light in a spectral range less than about 40 nm full width at half maximum (FWHM).

26. The composition of claim 25, wherein the monodisperse particle population is characterized in that when irradiated the population emits light in a spectral range less than about 25 nm full width at half maximum (FWHM).

27. The composition of claim 24, wherein the monodisperse particle population is characterized in that it exhibits no more than about a 10% rms deviation in the diameter of the core.

28. The composition of claim 27, wherein the monodisperse particle population is characterized in that it exhibits no more than about 5% rms deviation in the diameter of the core.

29. The composition of claim 1, wherein the ligand comprises the multidentate molecule, the multidentate molecule having structural formula (II),

(II)

wherein:

Y is the hydrophilic moiety;

Z is a hydrophobic region having a backbone of at least six atoms; and

X and X' are the same or different and are selected from the group of S, N, P and O=P, or are linked together to form a 5-membered to 8-membered ring upon coordination to the nanocrystal surface.

30. The composition of claim 1, wherein the ligand comprises the multidentate molecule, the multidentate molecule having structural formula (III),

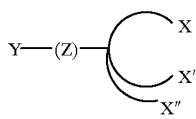

wherein
- Y is the hydrophilic moiety;
- Z is a hydrophobic region having a backbone of at least six atoms; and
- X, X' and X" are the same or different and are selected from the group of S, N, P and O=P, or are linked together to form a 5-membered to 8-membered ring upon coordination to the nanocrystal surface.

31. A composition, comprising
   a) a water-soluble semiconductor nanocrystal comprising
      i) a core comprising a first semiconductor material, the core being a member of a monodisperse particle population, and
      ii) a core-overcoating shell comprising a second semiconductor material;
   b) a ligand having a first portion comprising at least one linking group and a second portion comprising a hydrophilic group, wherein the linking group is linked to the nanocrystal; and
   c) a first member of a binding pair linked to the second portion of the linking agent.

32. The composition of claim 31, wherein the nanocrystal core is a Group II–VI, Group III–V or Group IV semiconductor.

33. The composition of claim 31, wherein the monodisperse particle population is characterized in that when irradiated the population emits light in a spectral range less than about 40 nm full width half maximum (FWHM).

34. The composition of claim 33, wherein the monodisperse particle population is characterized in that when irradiated the population emits light in a spectral range less than about 25 nm full width at half maximum (FWHM).

35. The composition of claim 31, wherein the monodisperse particle population is characterized in that it exhibits no more than about 10% rms deviation in the diameter of the core.

36. The composition of claim 35, wherein the monodisperse particle population is characterized in that it exhibits no more than about 5% rms deviation in the diameter of the core.

37. The composition of claim 31, wherein the core comprises CdS, CdSe, CdTe, ZnS, ZnSe, ZnTe, MgTe, GaAs, GaP, GaSb, GaN, HgS, HgSe, HgTe, InAs, InP, InSb, InN, AlAs, AlP, AlSb, AlS, PbS, PbSe, Ge, Si, an alloy thereof, or a mixture thereof.

38. The composition of claim 37, wherein the shell comprises ZnO, ZnS, ZnSe, ZnTe, CdO, SdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, an alloy thereof, or a mixture thereof.

39. The composition of claim 31, wherein the core is CdSe and the shell is ZnS.

40. The composition of claim 39, wherein the core is a member of a monodisperse particle population.

41. The composition of claim 40, wherein the monodisperse particle population is characterized in that when irradiated the population emits light in a spectral range less than about 40 nm full width at half maximum (FWHM).

42. Teh composition of claim 41, wherein the monodisperse particle population is characterized in that when irradiated the population emits light in a spectral range less than about 25 nm full width at half maximum (FWHM).

43. The composition of claim 40, wherein the monodisperse particle population is characterized in that it exhibits no more than about a 10% rms deviation in the diameter of the core.

44. The composition of claim 43, wherein the monodisperse particle population is characterized in that it exhibits no more than about 5% rms deviation in the diameter of the core.

45. The composition of claim 31, wherein the ligand comprises a molecule having structural formula (I),

or a salt thereof, wherein:
- X is the first portion of the ligand and is S, N, P or O=P;
- n is greater than of equal to 6; and
- z and y are selected to satisfy the valence requirements of X.

46. The composition of claim 45, wherein the first portion of the ligand comprises a moiety selected from the group consisting of amines, thiols, phosphines, phosphine oxides, and amine oxides.

47. The composition of claim 31, wherein the ligand comprises a molecule having structural formula (II),

wherein:
- Y is the hydrophilic moiety;
- Z is a hydrophobic region having a backbone of at least six atoms;
- X and X' are individually or together the linking groups, are the same or different and are selected from the group of S, N, P and O=P, or are linked together to form a 5-membered to 8-membered ring upon coordination to the nanocrystal surface.

48. The composition of claim 31, wherein the ligand comprises a molecule having structural formula (III),

wherein:
- Y is the hydrophilic moiety;
- Z is a hydrophobic region having a backbone of at least six atoms;
- X, X' and X" are individually or together linking groups, are the same or different and are selected from the group of S, N, P and O=P, or are linked together to form a 5-membered to 8-membered ring upon coordination to the nanocrystal surface.

49. The composition of claim 4, wherein the hydrophilic group is selected from the group consisting of a carboxylate, a sulfonate, a phosphate polyethylene glycol or other polyol, an ammonium salt, hydroxide, an alkoxide, phosphate and phosphonate.

50. The composition of claim 31, wherein the first member is a protein, an oligonucleotide, an enzyme inhibitor, a polysaccharide or a small molecule having a molecular weight of less than about 1500 grams/mole.

51. The composition of claim 31, wherein the first member is an antibody, avidin, streptavidin, biotin or anti-digoxiginen.

52. A composition, comprising
   a) a water-soluble semiconductor nanocrystal comprising
      i) a core comprising a first semiconductor material; and
      ii) a core-overcoating shell comprising a second semiconductor material;
   b) a ligand having a first portion comprising at least one linking group and a second portion comprising a hydrophilic group, wherein the linking group is linked to the nanocrystal; and
   c) a first member of a binding pair linked to the second portion of the linking agent, wherein the ligand comprises a multidentate molecule or a molecule having structural formula (I), $$H_zX((CH_2)_nCO_2H)_y \qquad (I)$$

or a salt thereof,
   wherein:
   X is the first portion of the ligand and is N, P or O=P;
   n is greater than of equal to 6; and
   z and y are selected to satisfy the valence requirements of X.

53. The composition of claim 52, wherein the first portion of the ligand comprises a moiety selected from the group consisting of amines, thiols, phosphines, phosphine oxides, and amine oxides.

54. The composition of claim 52, wherein the first member is a protein, an oligonucleotide, an enzyme inhibitor, a polysaccharide or a small molecule having a molecular weight of less than about 1500 grams/mole.

55. The composition of claim 52, wherein the first member is an antibody, avidin, streptavidin, biotin or anti-digoxiginen.

56. The composition of claim 62, wherein the link between the first member of the binding pair and the nanocrystal is an interaction selected from the group consisting of covalent, noncovalent, hydrophobic, hydrophilic, electrostatic, magnetic or coordination through a metal complex.

57. The composition of claims 52, wherein the nanocrystal core is a Group II–VI, Group III–V or Group IV semiconductor.

* * * * *